(12) United States Patent
Shores et al.

(10) Patent No.: US 7,799,020 B2
(45) Date of Patent: Sep. 21, 2010

(54) NEAR-INSTANTANEOUS RESPONSIVE CLOSED LOOP CONTROL ELECTROSURGICAL GENERATOR AND METHOD

(75) Inventors: Ronald B. Shores, Greenwood Village, CO (US); Brian C. Stuebe, Broomfield, CO (US)

(73) Assignee: ConMed Corporation, Utica, NY (US)

(*) Notice: Subject to any disclaimer, the term of this patent is extended or adjusted under 35 U.S.C. 154(b) by 1024 days.

(21) Appl. No.: 11/541,819

(22) Filed: Oct. 2, 2006

(65) Prior Publication Data
US 2008/0082095 A1 Apr. 3, 2008

(51) Int. Cl.
*A61B 18/18* (2006.01)
(52) U.S. Cl. .......................... 606/38; 606/34
(58) Field of Classification Search ............. 606/32–38, 606/20–52
See application file for complete search history.

(56) References Cited

U.S. PATENT DOCUMENTS

| | | | |
|---|---|---|---|
| 5,599,344 A | 2/1997 | Paterson | |
| 5,976,128 A | 11/1999 | Schilling et al. | |
| 6,142,992 A * | 11/2000 | Cheng et al. | 606/34 |
| 6,296,636 B1 * | 10/2001 | Cheng et al. | 606/32 |
| 6,663,623 B1 | 12/2003 | Oyama et al. | |
| 6,942,660 B2 | 9/2005 | Pantera et al. | |
| 2005/0177150 A1 * | 8/2005 | Amoah et al. | 606/34 |
| 2005/0197657 A1 * | 9/2005 | Goth et al. | 606/41 |

FOREIGN PATENT DOCUMENTS

| | | |
|---|---|---|
| WO | WO 96/19152 A1 | 6/1996 |
| WO | 2005/048809 A1 | 6/2005 |
| WO | 2005/112775 A1 | 12/2005 |

OTHER PUBLICATIONS

UK Intellectual Property Office, Search Report, Jan. 16, 2008.
UK Intellectual Property Office Search and Examination Report for Application No. GB0718537.4, dated Jun. 24, 2009, 3 pages.
UK Intellectual Property Office Combined Search and Examination Report for Application No. GB0806711.8, dated Aug. 15, 2008, 3 pages.
UK Intellectual Property Office Search Report for Application No. GB0718537.4, dated Jan. 17, 2008, 3 pages.
UK Intellectual Property Office Examination Report for Application No. GB0718537.4, dated Aug. 15, 2008, 2 pages.
UK Intellectual Property Office, Examination Report under Section 18(3), Dec. 21, 2009, 4 pages.

* cited by examiner

*Primary Examiner*—Linda C Dvorak
*Assistant Examiner*—Amanda Scott
(74) *Attorney, Agent, or Firm*—John R. Ley

(57) ABSTRACT

An electrosurgical generator has a control system formed by an array of logic gates programmed to execute mathematical algorithms for regulating at least one parameter of output power, output voltage or output current of an output electrosurgical signal in a closed loop response to sensed values of the output voltage and the output current.

37 Claims, 13 Drawing Sheets

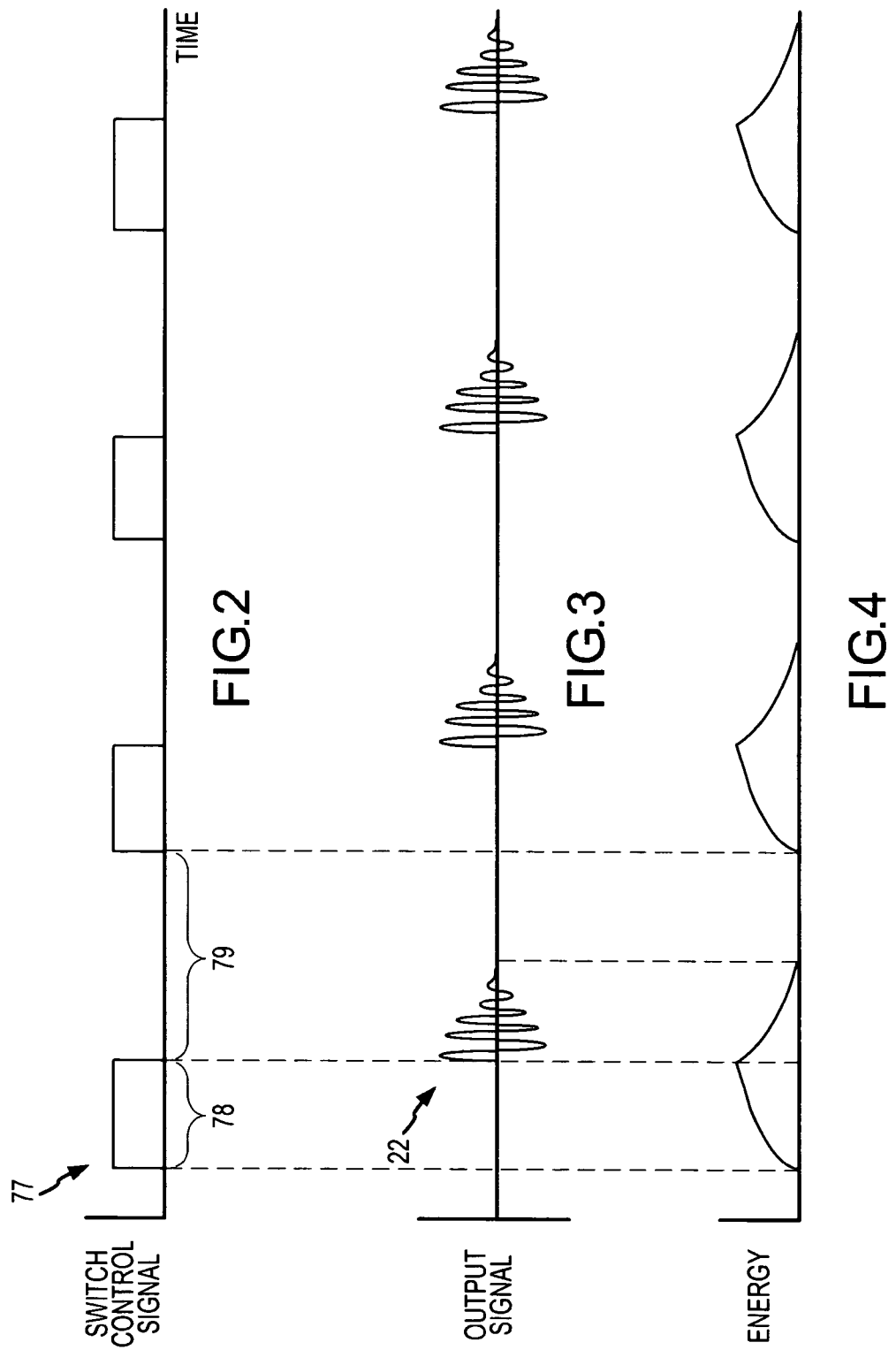

$$V_{OUT}(S) = \frac{(K_{snv1}S^2 + K_{snv2}S + K_{snv3})}{(K_{sndv1}S^2 + K_{sdv2}S + K_{sdv3})} V_{IN}(S) + \frac{(K_{sni1}S^2 + K_{sni2}S + K_{sni3})}{(K_{sdi2}S + K_{sdi3})} I_{IN}(S)$$

136 ⬈

WHERE:

$K_{snv1} = L_{ls} \cdot R_{ser/shunt} \cdot C_{series} + N^2 \cdot L_{mag} \cdot R_{ser/shunt} \cdot C_{series}$ $K_{snv2} = N^2 \cdot R_{mag} \cdot R_{ser/shunt} \cdot C_{series} + R_{ls} \cdot R_{ser/shunt} \cdot C_{series} + N^2 \cdot L_{mag} + L_{ls}$ $K_{snv3} = R_{ser/shunt} + R_{ls} + N^2 \cdot R_{mag}$ $K_{sdv1} = N \cdot L_{mag} \cdot R_{ser/shunt} \cdot C_{series}$ $K_{sdv2} = N \cdot L_{mag} + N \cdot R_{mag} \cdot R_{ser/shunt} \cdot C_{series}$ $K_{sdv3} = N \cdot R_{mag}$ $K_{sni1} = L_{ls} \cdot R_{ser/shunt} \cdot C_{series}$ $K_{sni2} = L_{ls} + R_{ls} \cdot R_{ser/shunt} \cdot C_{series}$ $K_{sni3} = R_{ser/shunt} + R_{ls}$ $K_{sdi2} = N \cdot R_{ser/shunt} \cdot C_{series}$ $K_{sdi3} = N$

FIG.8

$$V_{OUT}(Z) = \frac{(K_{znv1}Z^2 + K_{znv2}Z + K_{znv3})}{(K_{zdv1}Z^2 + K_{zdv2}Z + K_{zdv3})} V_{IN}(Z) + \frac{(K_{zni1}Z^2 + K_{zni2}Z + K_{zni3})}{(K_{zdi1}Z^2 + K_{zdi2}Z + K_{zdi3})} I_{IN}(Z)$$

$$V_{OUT}[n] = \frac{K_{znv1}}{K_{zdv1}} V_{IN}[n] + \frac{K_{znv2}}{K_{zdv1}} V_{IN}[n-1] + \frac{K_{znv3}}{K_{zdv1}} V_{IN}[n-2] + \ldots$$

$$\frac{K_{zni1}}{K_{zdi1}} I_{IN}[n] + \frac{K_{zni2}}{K_{zdi1}} I_{IN}[n-1] + \frac{K_{zni3}}{K_{zdi1}} I_{IN}[n-2] + \ldots$$

$$- (K_{zdv2} + K_{zdi2}) V_{OUT}[n-1] - (K_{zdv3} + K_{zdi3}) V_{OUT}[n-2]$$

$x[n] = V_{IN}[n] + I_{IN}[n]$ $\vdots$ $x[n-3] = V_{IN}[n-3] + I_{IN}[n-3]$ $d[n] = I_{OUT}[n]$ $$I_{OUT}(z) = \frac{(C_{znv0}z^3 + C_{znv1}z^2 + C_{znv2}z + C_{znv3})}{(C_{zdv0}z^3 + C_{zdv1}z^2 + C_{zdv2}z + C_{zdv3})}V_{IN}(z) + \frac{(C_{zni0}z^3 + C_{zni1}z^2 + C_{zni2}z + C_{zni3})}{(C_{zdi0}z^3 + C_{zdi1}z^2 + C_{zdi2}z + C_{zdi3})}I_{IN}(z)$$

FIG. 12 ↗ 146

$$I_{OUT}[n] = \left(\frac{C_{znv0}}{C_{zdv0}}\right)V_{IN}[n] + \left(\frac{C_{znv1}}{C_{zdv0}}\right)V_{IN}[n-1] + \left(\frac{C_{znv2}}{C_{zdv0}}\right)V_{IN}[n-2] + \left(\frac{C_{znv3}}{C_{zdv0}}\right)V_{IN}[n-3] + \left(\frac{C_{zni0}}{C_{zdi0}}\right)I_{IN}[n] + \left(\frac{C_{zni2}}{C_{zdi0}}\right)I_{IN}[n-2] + \left(\frac{C_{zni3}}{C_{zdi0}}\right)I_{IN}[n-3] - (C_{zdv1} + C_{zdi1})I_{OUT}[n-1] - (C_{zdv2} + C_{zdi2})I_{OUT}[n-2] - (C_{zdv3} + C_{zdi3})I_{OUT}[n-3]$$

$$V_{OUT}(z) = \frac{(K_{znv0}z^3 + K_{znv1}z^2 + K_{znv2}z + K_{znv3})}{(K_{zdv0}z^3 + K_{zdv1}z^2 + K_{zdv2}z + K_{zdv3})}V_{IN}(z) + \frac{(K_{zni0}z^3 + K_{zni1}z^2 + K_{zni2}z + K_{zni3})}{(K_{zdi0}z^3 + K_{zdi1}z^2 + K_{zdi2}z + K_{zdi3})}I_{IN}(z)$$

FIG. 14 ↗ 148

$$V_{OUT}[n] = \left(\frac{K_{znv0}}{K_{zdv0}}\right)V_{IN}[n] + \left(\frac{K_{znv1}}{K_{zdv0}}\right)V_{IN}[n-1] + \left(\frac{K_{znv2}}{K_{zdv0}}\right)V_{IN}[n-2] + \left(\frac{K_{znv3}}{K_{zdv0}}\right)V_{IN}[n-3] + \left(\frac{K_{zni0}}{K_{zdi0}}\right)I_{IN}[n] + \left(\frac{K_{zni2}}{K_{zdi0}}\right)I_{IN}[n-2] + \left(\frac{K_{zni3}}{K_{zdi0}}\right)I_{IN}[n-3] - (K_{zdv1} + K_{zdi1})V_{OUT}[n-1] - (K_{zdv2} + K_{zdi2})V_{OUT}[n-2] - (K_{zdv3} + K_{zdi3})V_{OUT}[n-3]$$

FIG. 15 ↗ 149

NEAR-INSTANTANEOUS RESPONSIVE CLOSED LOOP CONTROL ELECTROSURGICAL GENERATOR AND METHOD

CROSS REFERENCE TO RELATED APPLICATIONS

This invention is related to an invention for Electrosurgical Generator and Method for Simulating Output Signals, described in U.S. patent application Ser. No. 11/541,880 which is filed concurrently herewith by the present inventors and assigned to the assignee of the present invention. The disclosure of this concurrently-filed U.S. patent application is incorporated herein by this reference.

FIELD OF THE INVENTION

This invention relates to electrosurgery, and more specifically, to a new and improved electrosurgical generator and method which obtains nearly instantaneous closed loop feedback regulation to accurately and rapidly control electrosurgical power, voltage and current output signals. Preferably, the invention uses an array of logic gates to accomplish substantially all of the feedback and regulation functionality, thereby achieving the near-instantaneous responsiveness and enhanced performance.

BACKGROUND OF THE INVENTION

In broad terms, electrosurgery is the application of a high-voltage, high-frequency (HF) or radio-frequency (RF) output waveform to tissue to achieve a surgical effect. Tissue is cut, coagulated by stopping blood flow, or simultaneously cut and coagulated, depending upon the characteristics of the electrosurgical output signal. To achieve cutting, the output signal is substantially continuous. To achieve coagulation, the output signal is delivered in bursts with each burst defined by a duty cycle in which the on-time of the duty cycle is substantially less in time duration than the off-time. To achieve simultaneous cutting and coagulation, the output signal is also delivered in bursts, but the on-time and the off-time of the duty cycle are comparable in time to each other, or the on-time may exceed the off-time. The electrosurgical output signal is delivered to the tissue from an active electrode of an applicator or handpiece that is manipulated by the surgeon. The output signal is conducted to the electrode of the applicator over a conductor extending from the electrosurgical generator to the applicator or handpiece.

The load into which the electrosurgical output signal is delivered varies substantially during a surgical procedure due to large and almost instantaneous changes in the point-to-point resistance or impedance of the tissue encountered. For example, a highly fluid-perfused tissue, such as the liver, may exhibit a resistance or impedance in the neighborhood of 10-20 ohms while other tissues, such as skin or bone marrow, may have an impedance in the neighborhood of 1000 to 2000 ohms. When the active electrode passes from low impedance tissue into high impedance tissue, less current is momentarily delivered to the high impedance tissue thereby immediately degrading or inhibiting the desired electrosurgical effect. On the other hand, when the active electrode passes from high impedance tissue into low impedance tissue, high current is momentarily delivered into the low impedance tissue and a high current may create excess tissue damage. The variable impedance characteristics of the tissue require the electrosurgical generator to deliver and control relatively wide variations of power on essentially an instantaneously changing basis.

The practical effects of load variations resulting from the rapidly changing tissue resistance or impedance and the need to regulate a high-frequency, high-voltage electrosurgical output signal, create substantial limitations on the performance of an electrosurgical generator. If the control system of the electrosurgical generator cannot respond to the rapidly changing conditions encountered during electrosurgery, the output power regulation may not be sufficient to avoid unintended effects. Signals supplied by sensors of the electrosurgical output signal may not be processed quickly enough to be of effective use in regulating the output power. A control loop time lag or phase lag, which is that time between acquiring the sensed signals and making an adjustment in the output signals, maybe so long that a response cannot be achieved quickly enough to obtain or maintain the desired effect. The control loop time or phase lag is dependent upon many factors, but a principal factor relates to the speed at which the output voltage and current signals may be derived and processed into usable feedback and output control signals. The same circumstance also applies with respect to monitoring other output-related factors, such as tissue impedance, which must be calculated based on the instantaneous values of output voltage and current signals.

In addition to a rapid response time, the most effective control system for an electrosurgical generator should recognize the difference between real power and reactive or imaginary power. Real power produced by an electrosurgical generator creates the electrosurgical effect, while reactive power has no immediate electrosurgical effect. Reactive power is a consequence of the capacitive or inductive reactance of the entire system, principally including the output circuit to and from the patient.

If an electrosurgical generator uses a power feedback control system, a common approach to regulating output power is based on apparent power, rather than real power. Apparent power is the vector sum of the real and reactive power. Reactive power contributes to apparent power, but reactive power does not create the electrosurgical effect. Real power represents what can be expected as the electrosurgical effect, and apparent power is always more than the real power because of the reactive or imaginary contribution to apparent power. The difference between the power expected and the power delivered during electrosurgery can be substantial and important in achieving a satisfactory electrosurgical effect.

Distinguishing between real and apparent power requires knowledge of accurate output voltage and current values, and the relation or phase angle of the output voltage and current waveforms. Most typical electrosurgical generators do not have the capability to acquire or process such phase angle information, because to do so involves a complex control system with a fast measuring system. Moreover, the components of many control systems and the functionality of those control systems cannot perform or respond quickly enough to provide the necessary information to distinguish between real and apparent power. Indeed, many electrosurgical generators are open ended, and as such, have no capability to regulate output power using feedback.

A feedback control system based upon apparent power can sometimes degrade electrosurgical effects. For example, in endoscopic applications where a substantial amount of capacitance exists due to conducting the electrosurgical output signal within a relatively long endoscope, a significant portion of the apparent delivered power will be reactive or imaginary power. The substantial capacitance created by the endoscope must be charged with power and that component of the output power becomes reactive or imaginary. The diminished real power component of the output power might be insufficient to achieve the desired surgical effect. Another example involves the situation where both the apparent power and the real power are below the desired power output selected by the surgeon. In this situation, as the control system increases the power to the desired output power, because apparent power is greater in magnitude than real power, the control system will fail to ever deliver enough real power. In still other cases involving patient circuits with a high amount of reactance, such as minimally invasive procedures where the electrosurgical instruments are inserted inside of an endoscope or a laparoscope, regulation on the basis of apparent power may in some cases actually result in the delivery of more than the desired amount of power. The stored reactive power may be delivered as real power at unexpected times. In those open ended electrosurgical generators which have no feedback control, any load reactance is one more energy storage component which must be charged. Storing the added reactance with energy adds to the potential that the reactance will deliver that added power under unexpected circumstances. These and other exemplary cases of failing to distinguish between apparent power and real power during electrosurgery raise the risk of unintended surgical effects, diminished effectiveness of the surgical effect, and longer times required to complete the surgical procedure.

SUMMARY OF THE INVENTION

The present invention provides a closed loop feedback control system for an electrosurgical generator which regulates an electrosurgical output parameter of power, voltage or current while achieving a rapid response time and enhanced regulation under conditions of variable tissue resistance, variable output circuit reactance, and rigorous power delivery conditions. The benefits of the invention are achieved, in substantial part, by using an array of logic gates to execute the mathematical algorithms that implement the closed loop feedback control system. Near-instantaneous feedback is obtained for rapid and precise regulation of the output parameter, including real power.

One aspect of the invention involves an electrosurgical generator having a control system which comprises an array of logic gates programmed to execute mathematical algorithms for regulating at least one parameter of output power, output voltage or output current of an output electrosurgical signal in a closed loop response to sensed values of the output voltage and the output current of the output signal.

Another aspect of the invention involves a method for regulating at least one parameter of output power, output voltage or output current of an output electrosurgical signal by executing mathematical algorithms programmed into an array of logic gates which define a closed loop response to sensed values of the output voltage and the output current of the output signal.

A further aspect of the invention involves an electrosurgical generator which delivers an electrosurgical output signal and which has a closed loop control system. The closed loop control system comprises an output signal simulator, an output value calculator and an output controller. The output signal simulator calculates simulated values representative of output voltage and output current of the output signal. The output value calculator which calculates parameter values from the simulated values, and the parameter values relate to at least one parameter of output power or output voltage or output current of the output signal. The output controller calculates a feedback error signal and a control signal from the parameter values. The control signal regulates at least one parameter of output power or output voltage or output current of the output signal. The calculations are performed by mathematical algorithms executed by the output signal simulator, the output value calculator and the output controller. The output signal simulator and the output value calculator comprise an array of logic gates programmed to execute the mathematical algorithms of the output signal simulator and the output value calculator. As a subsidiary aspect, the output controller may also comprise an array of logic gates programmed to execute the mathematical algorithms of the output controller.

Subsidiary aspects of the invention include executing the programmed algorithms by the array of logic gates to simulate the values of the output voltage and output current in response to signals derived other than by directly sensing the values of output voltage and output current, to derive positive and negative values of the output voltage and the output current at simultaneously-related instants and calculate positive and negative values of output power from the values of the output voltage and output current, to calculate the real power output of the electrosurgical output signal by multiplying each instance of the positive and negative sensed values of the output voltage and output current, to define an output load curve of output power relative to load resistance into which the output power is delivered, to execute the programmed algorithms by numerical calculations, to regulate with respect to power and real power, and others.

A more complete appreciation of the present disclosure and its scope, and the manner in which it achieves the above and other improvements, can be obtained by reference to the following detailed description of presently preferred embodiments taken in connection with the accompanying drawings, which are briefly summarized below, and the appended claims.

BRIEF DESCRIPTION OF THE DRAWINGS

FIG. 2 is a waveform diagram illustrating a switch control signal generated by a control system of the electrosurgical generator shown in FIG. 1.

FIG. 3 is a waveform diagram on a common time axis with the signal shown in FIG. 2, illustrating an electrosurgical output signal created by the electrosurgical generator shown in FIG. 1.

FIG. 4 is a waveform diagram on a common time axis with the signals shown in FIGS. 2 and 3, illustrating energy in a resonant circuit of the electrosurgical generator shown in FIG. 1.

FIGS. 8-10 show equations employed in determining the simulation algorithm from the equivalent circuit shown in FIG. 7.

FIGS. 12-15 show equations employed in determining the simulation algorithm from the analytical model shown in FIG. 11.

DETAILED DESCRIPTION

Figure 1:
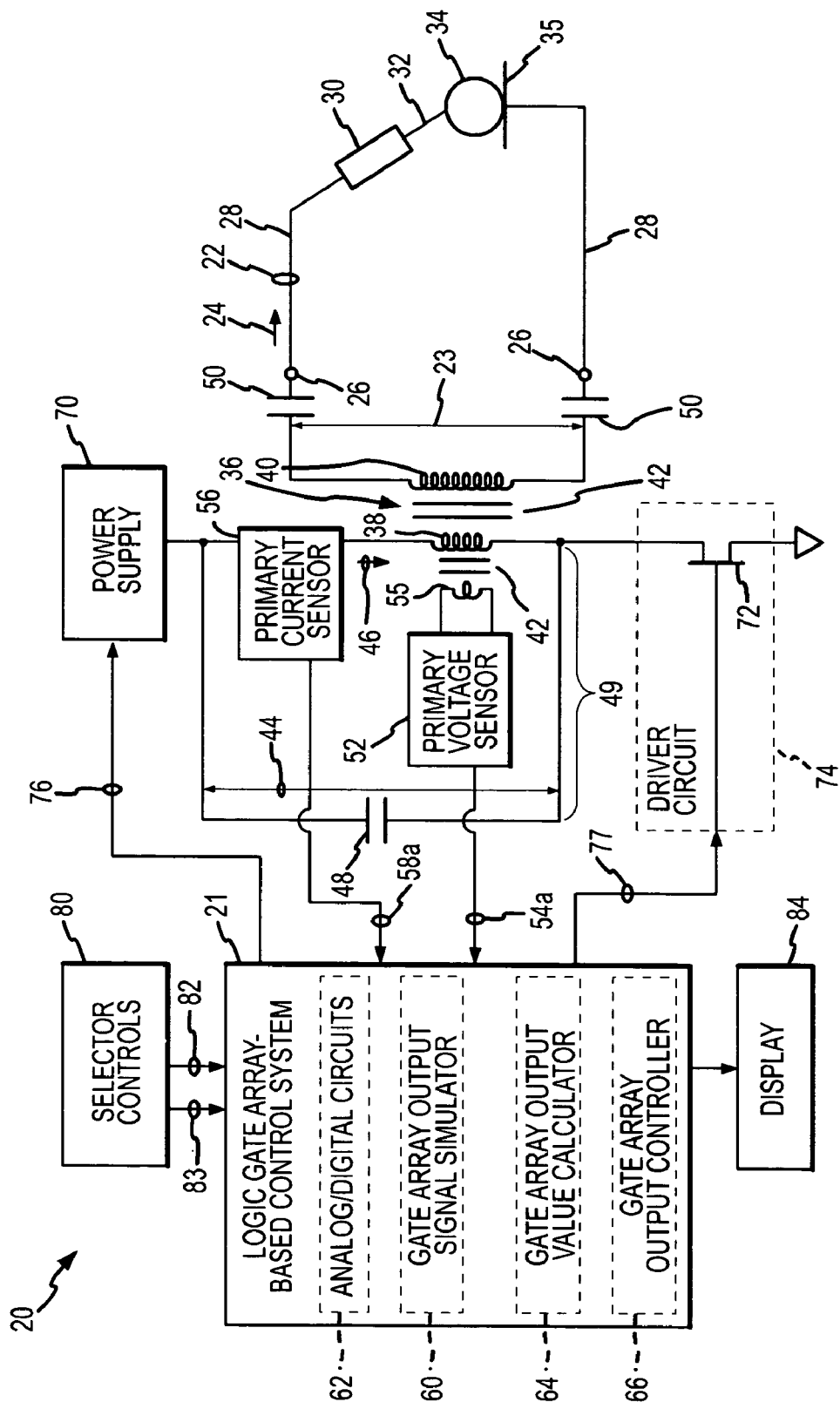
FIG. 1 is a block diagram of an electrosurgical generator incorporating the present invention.

An electrosurgical generator 20 which incorporates the present invention is shown in FIG. 1. An array of logic gates, such as a field programmable gate array (FPGA), is the basis of a logic gate array-based control system 21 which executes substantially all of the feedback and regulation functionality of the electrosurgical generator 20, or at least all of the intense and rapid computations necessary for rapid and effective output regulation. All the computations involved in controlling and regulating an electrosurgical output signal 22 from the electrosurgical generator 20 are performed mathematically, by either Boolean or numeric execution, from algorithms programmed into the logic gate array-based control system 21.

Using a logic gate array as basis for the control system 21 allows rapid, precise and reliable control over the electrosurgical output signal 22. The logic gate array-based control system 21 also achieves rapid and improved feedback response from the electrosurgical generator 20. The derivation and use of the feedback and control signals is delayed only by the gate delays and calculation clocking delays inherent in a gate array. Such gate and clocking delays consume considerably less time than those delays encountered from the typical digital and analog feedback control and regulation computations previously used in electrosurgical generators. Consequently, an improved almost-instantaneous response in output control and regulation is available. Moreover, an array of logic gates is more convenient to program and delivers better feedback control and output regulation, compared to software-driven computational controllers and microprocessors used in some electrosurgical generators. Using the array of logic gates as the basis for control system 21 also has the potential of facilitating manufacturing and reducing the cost of the electrosurgical generator 20, among other benefits.

The electrosurgical output signal 22 from the electrosurgical generator 20 is formed from an output voltage 23 and an output current 24. The output voltage 23 and output current 24 are delivered from output terminals 26 of the generator 20 and are conducted over leads or conductors 28 to an applicator or handpiece 30. The handpiece 30 includes an active electrode 32 through which the output voltage 23 and output current 24 are applied at a surgical site to patient 34 by the surgeon manipulating the handpiece 30. A return electrode 35 is connected to the patient 34 at a location remote from the surgical site. Another lead or conductor 28 connects the return electrode 35 to the electrosurgical generator 20 to complete an electrical circuit through the patient 34. When applied by the active electrode 32 to the tissue of the patient 34, the output voltage 23 and the output current 24 create a desired electrosurgical effect on the tissue, such as cutting, coagulating or simultaneous cutting and coagulating. Electrosurgical effects can also be achieved by combining comparably sized active and return the electrodes in a single, hemostat-like bipolar instrument and gripping the tissue between the electrodes while conducting the electrosurgical voltage 23 and current 24 through the gripped tissue, as is well known in bipolar electrosurgery.

The electrosurgical generator 20 includes an output transformer 36 having a primary winding 38 and a secondary winding 40 which are wrapped in coils around a core 42 of magnetic material. The electrosurgical output signal formed by the output voltage 23 and output current 24 are induced into and supplied by the secondary winding 40 in response to the application of an input or primary voltage 44 and an input or primary current 46 applied to and conducted by the primary winding 38. A capacitor 48 is connected in parallel with the primary winding 38 to form a conventional resonant circuit 49 with the primary winding 38. The resonant circuit 49 creates oscillations of the voltage 44 and the current 46 in the primary winding 38 at the natural frequency of the resonant circuit. The output voltage 23 and output current 24 alternate in the secondary winding 40 at the same frequency as the natural frequency of the resonant circuit. The natural frequency of the resonant circuit 49 establishes the high or radio frequency of the output voltage 23 and output current 24 of the electrosurgical output signal 22.

Isolating or blocking capacitors 50 are connected between the secondary winding 40 and the output terminals 26. The capacitors 50 isolate the patient from the electrosurgical generator 20 but conduct the high frequency output voltage 23 and current 24 to the tissue of the patient 34. The isolating capacitors 50 are typically required by safety regulations governing electrosurgery to ensure that very low frequency currents do not flow into the patient.

The electrosurgical generator 20 includes a primary voltage sensor 52 to sense the magnitude of the primary voltage 44 oscillating in the resonant circuit 49. The primary voltage sensor 52 supplies a primary voltage sense signal 54a which represents the magnitude of the primary voltage 44 across the primary winding 38. The primary voltage sensor 52 preferably uses an additional sense winding 55 wound on the core 42 adjacent to the primary winding 38, or alternatively, the primary voltage sensor 52 may use part of the primary winding 38 as an autotransformer (not shown). A primary current sensor 56 is also connected in series with the primary winding 38 in the resonant circuit 49. The primary current sensor 56 senses the magnitude of the primary current 46 flowing in the resonant circuit through the primary winding 38 and supplies a corresponding primary current sense signal 58a.

A gate array output signal simulator 60 of the control system accurately and reliably simulates the time values of the output voltage 23 and the output current 24 from the values of the primary voltage sense signal 54a and the primary current sense signal 58a. By doing so, the magnitude and spectral frequency content of the output signal 22 are not degraded by output sensors (not shown) which are connected to the secondary winding 40 of the output power transformer 36, as is the case in most other electrosurgical generators. Simulating values of the output voltage 23 and output current 24 without directly sensing those values is accomplished by executing one or more predetermined mathematical algorithms within the gate array output signal simulator 60. Output signal simulation involves intense and rapid signal and value computation which is performed by executing programmed mathematical algorithms by the array of logic gates in the output signal simulator 60. The mathematical simulation algorithms compensate for the distortion created by the transformer 36 when the primary voltage and current signals 44 and 46 induce the secondary voltage and current signals 23 and 24.

The primary voltage and current sense signals 54a and 58a, which are analog signals, are supplied to analog and digital circuitry 62 of the control system 21. The analog and digital circuitry 62 is not implemented by logic gates, because these circuit elements do not perform mathematical computations. Instead the analog and digital circuitry 62 conditions the analog signals and converts them into digital form. The digital forms of these signals are then utilized by the logic gate array of the control system 21 in the manner discussed herein.

A gate array output value calculator 64 of the control system 21 calculates values related to least one parameter of the output signal 22, such as real or apparent output power; RMS average output current, or RMS or instantaneous output voltage or other attributes and output power voltage or current. The calculation of the parameters of these output values is accomplished by executing mathematical algorithms within the logic gates which form the gate array output value calculator 64. Output signal simulation involves intense and rapid signal and value computation which is performed by executing programmed mathematical algorithms by the array of logic gates in the output value calculator 62. The calculation of the output values is based on the simulated values of the output voltage 23 and the output current 24 supplied by the gate array output signal calculator 60.

A gate array output controller 66 of the control system 21 controls or regulates the parameters of the output signal 22. The output controller 66 executes mathematical algorithms within a gate array to accomplish these functions. One or more calculated output values from the output value calculator 64 are supplied to the output controller 66, and selected ones of these calculated output values are used as feedback for developing error signals to control and regulate the primary voltage 44 and current 46 conducted by the resonant circuit 49, thus controlling and regulating the output signal 22. The functionality executed by the output controller 66 is less computationally intensive, because the signals and values may be calculated at a slower rate, since the output controller 66 controls and regulates the electrosurgical output signal at the much lower duty cycle repetition rate of that output signal. As a consequence, and although it is not preferred, a processor or controller which executes instructional code might perform the functions of the output controller rather than using an array of logic gates to do so.

The resonant circuit 49 is charged with electrical energy from a power supply 70 when a switch 72 of a driver circuit 74 is conductive. The control system 21 adjusts the energy available from the power supply 70 by supplying a power supply control signal 76 to the power supply 70. The control system 21 also controls the amount of energy transferred from the power supply 70 to the resonant circuit 49 by the characteristics of a switch control signal 77. The assertion of the switch control signal 77 causes the switch 72 to become conductive. Variations in the characteristics of the switch control signal 77 vary the conductivity of the switch 72, which in turn varies the amount of energy transferred to the resonant circuit 49. The adjustment of the power supply control signal 76 to vary the energy delivered from the power supply 70, and the adjustment of the characteristics of the switch control signal 77 to vary the amount of energy delivered to the resonant circuit 49, may occur separately or in conjunction with one another.

An exemplary switch control signal 77 is shown in FIG. 2. The switch control signal 77 takes the form of a duty cycle signal having an on-time 78 and an off-time 79. The switch control signal 77 repeats on a cyclical basis, with each cycle defined by one on-time 78 and one off-time 79. During the on-time 78, the assertion of the switch control signal 77 causes the switch 72 (FIG. 1) to conduct. During the off-time 79, the switch control signal 77 is not asserted and the switch 72 is nonconductive. When the switch 72 is conductive, from the power supply 70, energy charges the resonant circuit 49 and is stored in the capacitor 48 and, to a lesser extent, in the inductor formed by the primary winding 38 of the output transformer 36 (FIG. 1). The amount of charging energy delivered to the resonant circuit 49 is directly related to the on-time 78 of the switch control 77. Adjusting the on-time 78 results in a corresponding opposite change to the off-time 79, since each cycle of the switch control signal 77 occurs at a regular frequency established by the selected mode of operation of the electrosurgical generator 20.

During the off-time 79, the energy transferred into the resonant circuit 49 commences oscillating at the natural frequency of the resonant circuit 49, causing the primary voltage signal 44 and the primary current signal 46 to oscillate at that natural frequency. The transformer 36 induces the output voltage 23 and output current 24 of the electrosurgical output signal 22 from the energy oscillating in the resonant circuit 49. FIG. 3 illustrates the oscillations of the output signal 22 commencing immediately at the beginning of the off-time 79 of the switch control signal 77. The energy which charged the resonant circuit 49 during the on-time 78 is substantially dissipated during the off-time 79 as a result of the output signal 22 delivering that energy into the tissue of the patient 34 (FIG. 1). Consequently, the magnitude of the output signal 22 decays during the off-time 79, as shown in FIG. 3. Substantially all of the energy originally contained in the resonant circuit 49 is usually dissipated by the end of the off-time 79, as shown by the fully decayed oscillations of the output signal 22 at the end of the off-time 79.

The output controller 66 executes mathematical algorithms to establish and vary the on-time 78 of the switch control signal 77. By controlling the duration of the on-time 78, as illustrated in FIG. 4, the energy content of the resonant circuit 49 is controlled, which in turn controls the electrosurgical output signal 22. Adjustments in the on-time duration of the switch control signal 77 are caused by the feedback-derived control signals supplied by the output controller 66.

The output controller 66 also develops and supplies the control signal 76 to the power supply 70 to adjust and vary the amount of energy delivered from the power supply 70 to the resonant circuit 49 when the switch 72 is conductive. For example, the control signal 76 may adjust the voltage output from the power supply 70. By increasing the voltage, the amount of energy transferred during the on-time 78 of the switch control signal 77 is increased, even though the duration of the on-time 78 may remain the same. The output controller 66 derives power supply control signal 76 by executing mathematical algorithms and computations.

Other methods exist to alter the output power aside from the from those just discussed. In general, the switch 72 and the signal 78 may be from any power amplifier device and control signal that varies the energy transferred to the resonant circuit. Techniques for varying the energy transfer to the resonant circuit include a switch and a fixed frequency switch signal where the duty cycle on the switch signal varies the energy transfer, a switch and a fixed frequency switch signal where the supply voltage to the resonant circuit varies the energy transfer, a switch and a fixed pulse width switch signal where the pulse repetition frequency varies the energy transfer, a switch and a fixed pulse width switch signal where the supply voltage to the resonant circuit varies the energy transfer, a switch and a fixed frequency, fixed pulse width switch signal for varying the saturation voltage of the switch to vary the energy transferred, and a magnetic amplifier and a variable saturation threshold signal to an inductor which varies the energy transferred, among other things.

The electrosurgical generator 20 also includes conventional selector controls 80 which are connected to the control system 21, as shown in FIG. 1. The selector controls 80 include selection switches (not shown) which allow the desired power content of the output signal 22 over a range of loads to be selected and adjusted. Selecting the desired output power content results in the assertion of a power selection signal 82. The selector controls also include other selection switches (not shown) which allow the mode of operation of the electrosurgical generator to be selected. The selectable modes of operation are cutting, coagulation and simultaneous cutting and coagulation known as "blend." Selecting the desired mode of operation results in asserting a mode selection signal 83. The selector controls 80 supply the power and mode selection signals 82 and 83 to the control system 21.

By selecting the desired power content of the output signal 22 and the mode of operation, the initial parameter of the on-time 78 of the switch control signal 77 (FIG. 2) is established. The initial on-time parameter is used as the initial reference for further control and regulation. The power and mode selection signals 82 and 83 establish a load curve (FIG. 17) which becomes the reference for feedback power regulation executed by the output controller 66 of the control system 21 based on values of the output signal 22 supplied by the output value calculator 64. The difference between the reference and feedback signals constitutes an error signal from which an output control signal is derived to adjust the on-time 78 of the switch control signal 77 (FIG. 2). The mode selection also contributes to establishing the initial on-time parameter and may also establish the repetitive frequency of the switch control signal 77.

The selections and values from the selector controls 80, and possibly other values or factors derived by the control system 21, are displayed on a display 84 or otherwise made available for use by auxiliary equipment employed in an operating room.

The surgeon causes the electrosurgical generator 20 to deliver the electrosurgical output signal 22 by depressing a conventional finger switch (not shown) on the handpiece 30 or stepping on a conventional foot switch (not shown) connected to the electrosurgical generator. Each depression of one of the switches is referred to as an activation of the electrosurgical generator. In response to each activation, the control system 21 commences delivering the switch control signal 77, which causes the resonant circuit 49 to be charged with energy from the power supply 70 during the on-time 78 of the switch control signal 77, and the delivery of the electrosurgical output signal 22 during the off-time 79 of the switch control signal as previously described (FIGS. 2-4). The electrosurgical output signal 22 is delivered continuously according to the selected mode of operation while the electrosurgical generator is activated.

Figure 5:
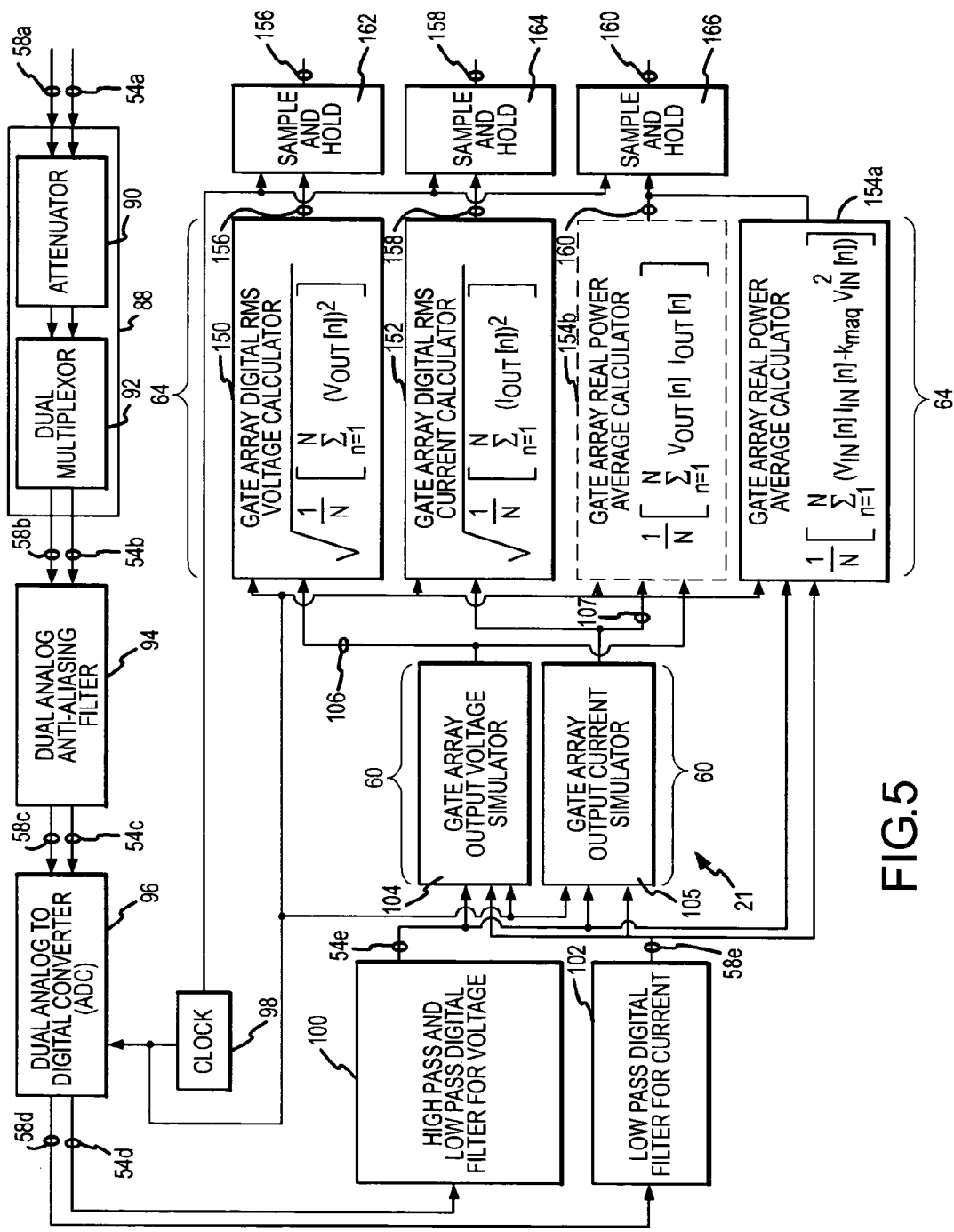
FIG. 5 is a block diagram showing analog and digital circuits, an output signal simulator and an output value calculator of a control system of the electrosurgical generator shown in FIG. 1.

More details of the output signal simulator 60, the analog and digital circuitry 62, and the output value calculator 64 of the control system 21, are shown in FIG. 5. The primary voltage sense signal 54a and the primary current sense signal 58a are supplied to an attenuator bank 88. The attenuator bank 88 is formed by an attenuator 90 and a dual multiplexer 92. The attenuator 90 attenuates the magnitude of the primary voltage sense signal 54a and the primary current sense signal 58a. The dual multiplexer 92 is set prior to activation of the electrosurgical generator and therefore does not change the output terminal connections to which its input signals are supplied. Consequently, the attenuator 88 supplies an attenuated primary voltage sense signal 54b and an attenuated primary current sense signal 58b.

The attenuated voltage and current sense signal 54b and 58b are supplied to a dual analog anti-aliasing filter 94. The anti-aliasing filter 94 is a low pass filter that generates a filtered primary voltage sense signal 54c and a filtered primary current sense signal 58c, after the undesired high-frequency components (especially higher order harmonics) have been removed from the attenuated signals 54b and 58b. The anti-aliasing filter 94 assures that the significant frequency components of the filtered signals 54c and 58c are below a predetermined upper frequency in order to prevent the creation of unintended aliased signals from the signals 54b and 58b, when those signals are subsequently converted into corresponding digital signals.

The filtered signals 54c and 58c are supplied to a dual analog to digital converter (ADC) 96 which is driven by a clock 98. The dual ADC 96 and clock 98 determine the sampling and conversion rate of the filtered analog primary voltage sense signal 54c and the filtered analog primary current sense signal 58c. The dual ADC 96 converts the filtered analog signals 54c and 58c to a digital primary voltage sense signal 54d and a digital primary current sense signal 58d, respectively.

The sampling rate established by the clock 98 is relatively high, due to the rapid computational speed of the logic gates of the system controller. The sampling rate can equal or exceed the Nyquist sampling criterion (two samples per cycle of the highest frequency of consequential energy in the output signal 22). However, it is also possible to use under-Nyquist sampling algorithms because, as shown in FIG. 3, each successive cycle of the output signal 22 is very similar to the preceding waveform. The similarity between subsequent repeating cycles allows sampling rates less than the Nyquist criterion to provide effective information for the output regulation of the present invention. Furthermore, as is discussed below, feedback control is not based entirely on a single cycle of an electrosurgical output signal 22 (FIG. 3), but rather is based on a number of successive cycles of the output signal 22. Even though under-Nyquist sampling criteria may prove satisfactory, sampling at or above the Nyquist criteria is preferred and is possible due to the computational rate of the array of logic gates used in the control system 21.

An important aspect of the sampling achieved by the ADC 96 is that the values of the output voltage 23 and the output current 24 (FIG. 1) are obtained at instants which are simultaneously related. Consequently, any differences in phase between the output voltage and the output current at each instant are determinable. Such phase differences also allow the determination of negative power output resulting from simultaneously-related, instantaneous, and respectively-different positive and negative values of output voltage and current. The sample values of the output voltage and output current may be obtained from simultaneous sampling, or it is possible to derive apparent simultaneously-related samples by sample interpolation techniques, some of which are also possible when using under-Nyquist sampling criteria. The control system must take into account the limitations of such interpolations. Recognizing the phase relationship and the positive and negative values of the output voltage and output current relative to each other on a simultaneously-related basis at times during each cycle of the electrosurgical output signal is one important basis for the improved output regulation available from the present invention. The phase relationship and the positive and negative values of the output voltage and output current also account for the difference between real and apparent power output in an electrosurgical output waveform, as understood from FIG. 6.

Figure 6:
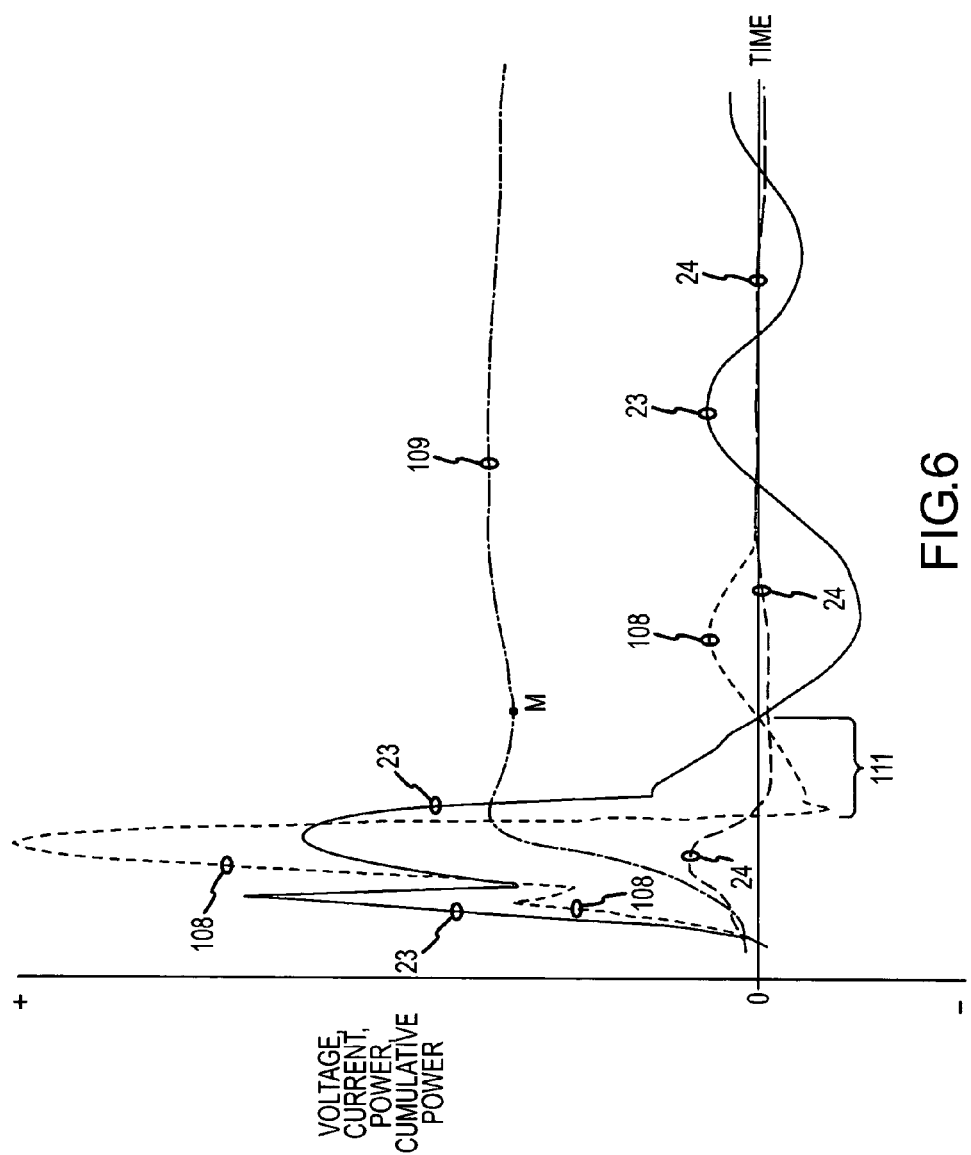
FIG. 6 is a graph showing exemplary waveforms of output voltage, output current, output power, and cumulative output power of the electrosurgical generator shown in FIG. 1.

Shown in FIG. 6 are waveforms of the output voltage 23 (shown as a solid line) and the output current 24 (medium dashed lines). The waveforms 23 and 24 are typical for the time period 79 (FIGS. 2 and 3) immediately after the resonant circuit 49 (FIG. 1) commences oscillating. The output voltage 23 and the output current 24 vary considerably relative to one another until the energy of the resonant circuit 49 (FIG. 1) is dissipated. A curve 108 shows the instantaneous power output, and a curve 109 shows the integral or cumulative amount of energy delivered, by short dashed lines and by dash and dot lines, respectively. During most but not all of the time period depicted in FIG. 6, the instantaneous power output waveform 108 indicates that a positive amount of power is delivered to the tissue as real power. However, because the output voltage and current 23 and 24 are out of phase, negative power is delivered during a time interval 111.

The negative power delivered during time interval 111 results from energy that is stored in external capacitance or inductance components connected to the output terminals 26 (FIG. 1), such as parasitic capacitance or inductive reactance. The electrosurgical generator has previously stored energy in these reactance elements, and then some or all of this energy is subsequently returned to the electrosurgical generator without creating an electrosurgical effect at the tissue. As shown in FIG. 6, the negative power during the time interval 111 results when the output current 24 is negative, indicating that current is flowing into the electrosurgical generator while there is a positive output voltage 23. The occurrence of negative power is also indicated by a small dip or minimum at point M in the cumulative output power curve 109.

Failing to recognize that negative output power occurs, such as during time interval 111, results in the negative power being attributed as part of the apparent power output of the electrosurgical generator. The electrosurgical generators typically fail to distinguish between apparent power output and real power output, because the typical calculation of output power involves an RMS calculation. An RMS calculation cannot take into consideration the negative power aspect of the current flowing back into the electrosurgical generator while the output voltage is positive. Real power output from the electrosurgical generator is the power that creates the electrosurgical effect, which is mostly heat in the tissue. Thus, real power is of primary interest from the electrosurgical effect perspective. On the whole, the real power delivered from the electrosurgical generator is shown by the positive values of the cumulative output power curve 109.

Shown in FIG. 5, the digital primary voltage sense signal 54d is conducted to a high pass and low pass digital filter 100 with signal compensation. The filter 100 eliminates the effect of residual energy stored in the isolation capacitors 50 (FIG. 1) at the end of an activation of the electrosurgical generator. The energy stored in the isolation capacitors can vary depending upon the technique of the surgeon and the mode of electrosurgical procedure. Without eliminating the effect of the residual stored energy in the capacitors 50, the simulation of the output voltage and current is less accurate. After high and low pass filtering and compensating the signal 54d, the high and low pass digital filter 100 supplies a filtered and compensated digital voltage signal 54e.

The digital primary current sense signal 58d is conducted to a low pass digital filter 102. The low pass filter 102 also prevents anti-aliasing. After low pass filtering the digital signal 58d, the low pass digital filter 102 supplies a filtered digital current signal 58e.

The components 88, 90, 92, 94, 96, 98, 100 and 102 form the analog and digital circuits 62 of the control system 21 (FIG. 1). The components 88, 90, 92, 94, 96, 98, 100 and 102 are conventional analog signal and digital signal processing elements used to convert the analog signals 54a and 58a into the digital signals 54e and 58e so those signals can be used by the gate array output signal simulator 60 (FIG. 1).

The output signal simulator 60 shown in FIG. 1 is formed by an output voltage simulator 104 and an output current simulator 105, both of which are shown in FIG. 5, and both of which are preferably executed by an array of logic gates. The digital voltage signal 54e and the digital current signal 58e are conducted to the output voltage simulator 104 and the output current simulator 105. The simulators 104 and 105 each respond to the signals 54e and 58e by executing mathematical simulation algorithms which simulate an accurate value of the output voltage 23 and the output current 24, based on the primary voltage 44 and the primary current 46 in the resonant circuit 49 (FIG. 1).

The simulated values of the output voltage 23 and the output current 24 (FIG. 1) are supplied as a simulated output voltage signal 106 and a simulated output current signal 107, respectively. The simulators 104 and 105 are implemented as an array of logic gates which have been programmed or interconnected to execute the mathematical simulation algorithms used by each simulator. The array of logic gates rapidly executes the mathematical simulation algorithms to supply the simulated output signals 106 and 107 almost instantaneously since those simulated signals are delayed only by the short gate delays and calculation clocking delay times associated with the digital logic gates. The presence and utility of the simulated output signals 106 and 107 are available considerably more rapidly than would be the case if other more time consumptive computations were used.

More details regarding the mathematical algorithms implemented by the gate array output voltage and current simulators 104 and 105 are discussed in conjunction with FIGS. 7-15.

Figure 7:
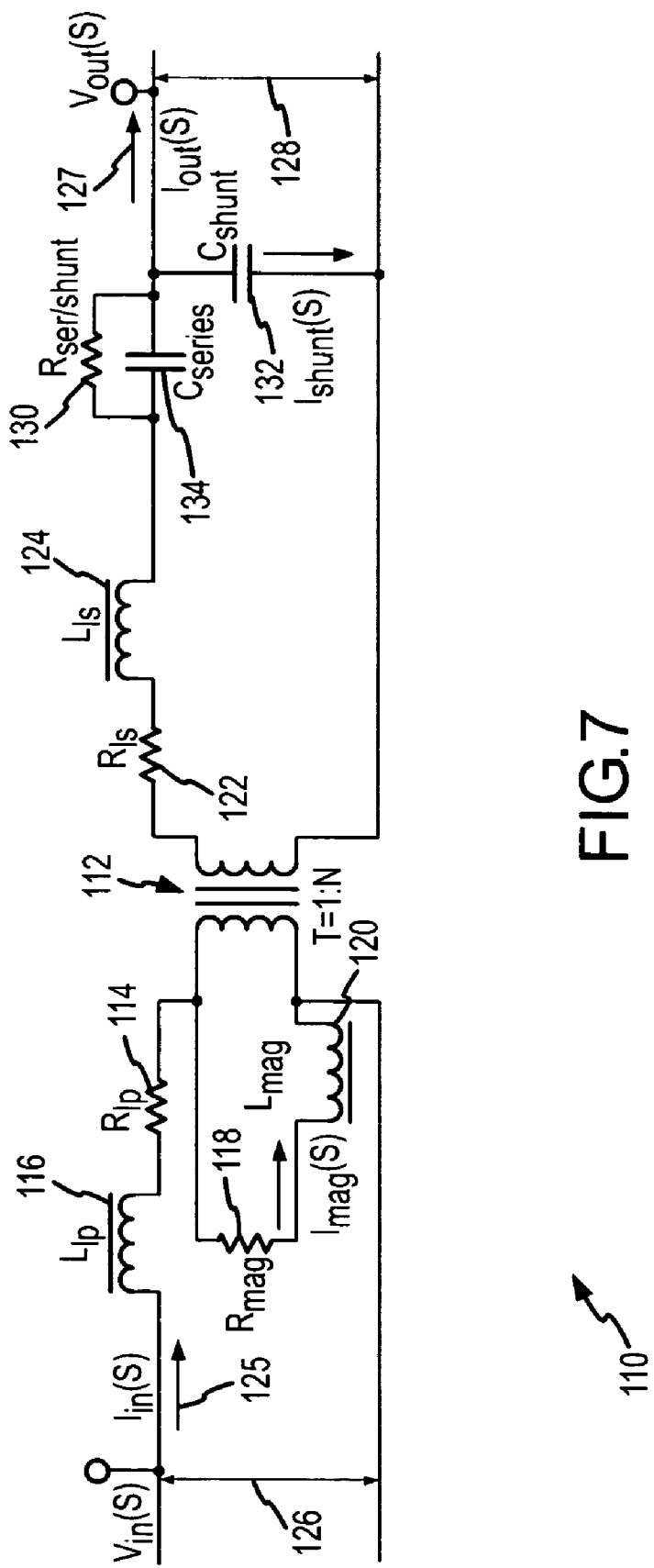
FIG. 7 is a lumped parameter equivalent circuit of an output circuit of the electrosurgical generator shown in FIG. 1, used to obtain a simulation algorithm executed by the output signal simulator shown in FIG. 5.

A number of different known mathematical algorithms can be executed by the simulators 104 and 105 to simulate accurate values of the output voltage and current signals 106 and 107. One advantageous algorithm for simulating output voltage is derived from a model of a lumped parameter, equivalent circuit 110 of an output circuit of the electrosurgical generator 20 formed by the output transformer 36 and the isolation capacitors 50 (FIG. 1). One such lumped parameter, equivalent circuit 110 is shown in FIG. 7. The use of equivalent circuits to model the non-ideal behavior of electronic circuit components is known, and the equivalent circuit 110 is one of many possible equivalent circuits that could be used to derive a response function for the output transformer 36 and the isolation capacitors 50 (FIG. 1). It is important to establish lumped parameters for the equivalent circuit which can be measured from the actual transformer and isolation capacitors which the equivalent circuit 110 models, because the accuracy of those measured values establishes the accuracy of the equivalent circuit model as the basis for the simulation algorithm. All of the elements of the equivalent circuit 110 are assumed to be ideal.

The portion of the basic lumped parameter equivalent circuit 110 which relates to the output transformer 36 (FIG. 1) is formed by a transformer 112, a primary leakage resistor ($R_{lp}$) 114, a primary leakage inductor ($L_{lp}$) 116, a magnetic resistor ($R_{mag}$) 118, a magnetic inductor ($L_{mag}$) 120, a secondary leakage resistor ($R_{ls}$) 122, and a secondary leakage inductor ($L_{ls}$) 124.

The primary leakage resistor 114 and the secondary leakage resistor 122 model the resistance encountered by AC currents $I_{in}(S)$ 125 conducted through the primary winding and $I_{out}(s)$ 127 conducted through the secondary winding, respectively. The resistance encountered by these AC currents through the windings 38 and 40 (FIG. 1) results in energy losses as heat, and these energy losses are commonly known as copper losses. The energy losses are reflected in a voltage drop from an input voltage $V_{in}(s)$ 126 to an output voltage $V_{out}(s)$ 128 of the equivalent transformer circuit 110.

The primary leakage inductor 116 and the secondary leakage inductor 124 model the flux leakage of the core 42 (FIG. 1). Leakage flux emanates from the core and fails to couple the primary winding 38 with the secondary winding 40 (FIG. 1). The inductors 116 and 124 in the equivalent circuit 110 introduce a phase shift between the current and voltage that is present at the windings 38 and 40 (FIG. 1). The effect of the phase shift is that the real power of the output signal delivered from the secondary winding 40 (FIG. 1) is diminished, because some of the apparent power is reactive power.

Real power and reactive power are combined through vector analysis (or a power triangle) to obtain apparent power. Only the real power produces an electrosurgical effect at the tissue of the patient 34 (FIG. 1). Reactive power does not produce an electrosurgical effect. The consumption of output power as reactive power may diminish the ability to achieve a desired electrosurgical effect, or may result in the storage of power in some types of electrosurgical accessories which is later released as real power under circumstances where an electrosurgical effect was not desired.

The magnetic resistor 118 and the magnetic inductor 120 account for core losses. To produce the magnetic flux within the core 42 (FIG. 1), an exciting current is required. The magnetic resistor 118, known as the core-loss resistance, accounts for the core-loss current, or the real component of the exciting current. The magnetic inductor 120, known as the magnetizing reactance, accounts for the magnetizing current in the core or the imaginary-component of the exciting current component.

The electrosurgical output signal of the output transformer 36 is a high or radio frequency signal (typically 350-600 kHz) that experiences rapidly changing transient conditions due to the highly variable impedance of the tissue through which the electrosurgical output signal is conducted. To correctly model the high frequency response characteristics of the output transformer 36 (FIG. 1), the equivalent circuit 110 must include additional elements to account for the parasitic capacitance characteristics of the power output transformer 36 and the isolation capacitors 50 (FIG. 1). These additional elements include a series shunt resistor ($R_{ser/shunt}$) 130 and a shunt capacitor ($C_{shunt}$) 132 and a series capacitor ($C_{series}$) 134. The series capacitor ($C_{series}$) 134 accounts for the capacitive effects of the isolating capacitors 50 (FIG. 1), and the series shunt resistor ($R_{ser/shunt}$) 130 models the inherent resistive effects of the isolating capacitors. The shunt capacitor ($C_{shunt}$) 132 models the parasitic capacitances that arise between the conductor coils that form the primary winding 38 and the secondary winding 40 (FIG. 1). Similar to the inductors 116, 120, and 124, the capacitors 132 and 134 introduce phase shifts between the currents and the voltages that are present on the primary winding and the secondary winding. In addition, the capacitances store energy and attenuate energy at different frequencies throughout the energy spectrum. Consequently, some of the input energy delivered by the power supply 70 (FIG. 1) is stored in the capacitors 132 and 134 until that stored energy is discharged during electrosurgery.

The output equivalent circuit 110, shown in FIG. 7, is used to derive a discrete-time function for the output transformer 36 (FIG. 1). The discrete-time function is then used to calculate the output response function of the transformer 36. To proceed in this manner, the values for the resistors 114, 118, 122, and 130, the values for the inductors 116, 120, and 124, and value for the capacitor 132 are determined experimentally. Any values experimentally determined to be negligible may be taken as zero when deriving the discrete-time function from the equivalent circuit. In one implementation, the values for the primary leakage resistor 114 and the primary leakage inductor 116 were set as zero, since their contributions were found experimentally to be negligible for the actual output transformer 36 (FIG. 1).

Figure 9:
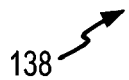
Figure 10:
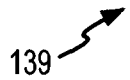

The approach to arriving at the discrete-time function by use of the equivalent circuit model 110 (FIG. 7) is shown in FIGS. 8-10.

By using standard circuit analysis techniques, the equivalent circuit model 110 yields the continuous-time, frequency-domain function 136 shown in FIG. 8. The continuous-time, frequency-domain function 136 provides the desired voltage output response $_{Out}(s)$ 128 (FIG. 7). The continuous-time, frequency-domain function consists of eleven constants, the input voltage variable $V_{in}(s)$ 126 (FIG. 7) and the input current variable $_{In}(s)$ 125 (FIG. 7). The values of the eleven constants are calculated from the experimentally determined values for the lumped parameter components of the equivalent circuit 110 (FIG. 7). The input voltage variable $V_{in}(s)$ 126 and the input current variable $_{In}(s)$ 125 (FIG. 7) are obtained from the digital voltage and current signals 54e and 58e (FIG. 5), respectively. The function 136 shown in FIG. 8 represents the Laplace transform of the equivalent circuit 110 (FIG. 7).

The function 136 shown in FIG. 8 is mathematically transformed into a discrete-time, frequency-domain function 138 as shown in FIG. 9, using recognized techniques for transforming continuous-time, frequency-domain functions into discrete-time, frequency-domain functions. Due to the fact that such transformations are not precise mathematical derivations, but instead involve numerical fitting techniques to minimize differences, the transformation shown in FIG. 9 results in twelve new constants rather than the previous eleven constants shown in FIG. 8. Conversely, a transformation which provides less close numerical minimization might involve a lesser number of constants, and will be less complex for computational execution. The input and output response variables of the function 138 are discrete values.

The output voltage simulator 104 (FIG. 5) requires that the input variables be in the time domain as opposed to the frequency domain. Thus, a final transformation is required to take the function from the discrete-time, frequency-domain shown in FIG. 9 to the discrete time, time-domain. As shown in FIG. 10, the final function 139 constitutes the mathematical simulation algorithm which is employed by the output voltage simulator 104 (FIG. 5) to obtain the output simulated voltage signal 106 (FIG. 5). After the final function 139 is obtained, it is programmed into the array of logic gates which form the output signal simulator 104.

Relating the discrete-time, time-domain function 139 shown in FIG. 10 to samples of the discrete values performed by ADC 96 (FIG. 5), the input samples $V_{in}[n]$ and $I_{in}[n]$ of the function 139 correspond to the filtered digital voltage signal 54e and filtered digital current signal 58e (FIG. 5), respectively. The input samples $V_{in}[n]$ and $I_{in}[n]$ are supplied at the regular and continuously occurring sampling point times [n]

at which the ADC 96 (FIG. 5) supplies new values of the filtered digital voltage signal 54e and filtered digital current signal 58e (FIG. 5). The sampling point times [n] are established by the clock 98 (FIG. 5). As is apparent from the function 139, at least three sequentially-occurring input samples (n, n−1, and n−2) of the input samples $V_{in}[n]$ and $I_{in}[n]$ are required to establish initial conditions before the function 139 will produce a meaningful value of $V_{out}[n]$. The value of $V_{out}[n]$ becomes the simulated voltage signal 106 (FIG. 5).

The mathematical algorithm represented by the function 139 is based on characteristics of the output transformer 36 and isolation capacitors 50 (FIG. 1). The accuracy of the simulation using the function 139 will depend on the accuracy and ability to experimentally determine or measure the parasitic and other characteristic values from the actual transformer and isolation capacitors for use in the equivalent circuit 110 (FIG. 7), since the twelve constants in the discrete-time function 139 (FIG. 10) are directly dependent upon these values. The extent of simulation error also relates to the amount of load attached to the transformer as the output circuit. In general, the simulation error tends to be lower for lesser output currents from the transformer into smaller loads, and the simulation error tends to be higher for greater output currents from the transformer into larger loads. However, the equivalent circuit modeling technique (FIGS. 7-10) of deriving a mathematical algorithm for simulating the output voltage has the advantage in general of providing less error under the circumstances, represented by function 139, where two input signals create one output signal and one of the two input signals is partially caused by the other. The primary current to the transformer is partially caused by the primary voltage and is partially caused by the output load.

The same mathematical algorithm, such as the discrete-time function 139 (FIG. 10), may be programmed and used in each voltage simulator 104 (FIG. 5) of every mass-produced electrosurgical generator if the characteristics among the individual power output transformers in all of the electrosurgical generators are approximately equal. Under such circumstances the need to individually program each simulator with a different mathematical algorithm is avoided. However, if significant variances in parametric values exist from one transformer to the next, the mathematical algorithm may need to be adjusted or re-determined for each individual transformer. In addition, because the loading characteristics may create variances in the simulation error, different mathematical algorithms may be used to simulate the response characteristics over different areas of a load curve, as may be understood from the following discussion. Thus, different simulation algorithms may be employed. Although different mathematical algorithms have been used with respect to the voltage simulator 104 (FIG. 5) as discussed above, the concepts involved in using different mathematical algorithms are also applicable to the current simulator 105 (FIG. 5) discussed below.

Another way of obtaining the simulation algorithm is an iterative numerical comparison of the digital voltage and current signals 54e and 58e (FIG. 5) over a range of load parameters. This iterative numerical comparison technique is one type of a system identification technique. System identification techniques are a specific form of adaptive signal processing, and they implement a numerical analysis process in which the observed inputs and outputs of an unknown or poorly-understood system are used to create a transfer function of that system. System identification techniques are useful to predict the behavior of the unknown or poorly-known system without first discovering the principles of that system. All that is required is the ability to gather and correlate relevant input and output signals and convert those signals into a form for comparison and manipulation by a microprocessor or computer.

Figure 11:
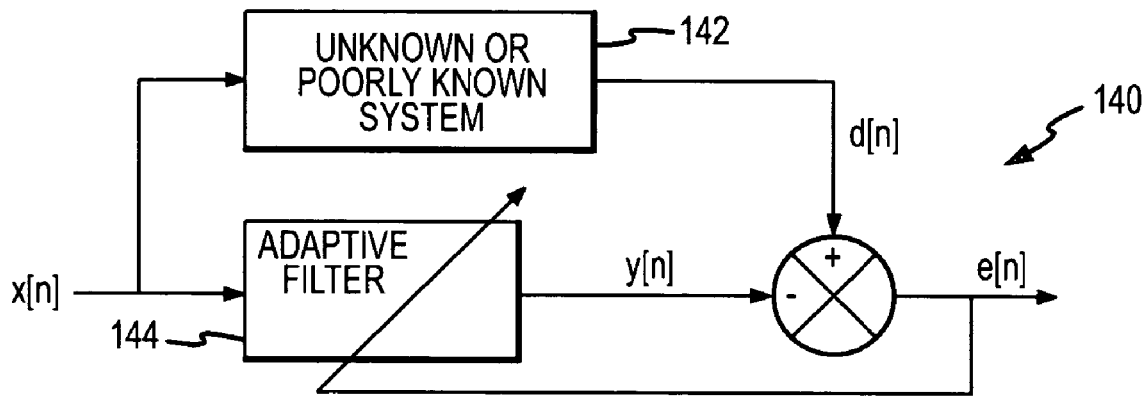
FIG. 11 is a block diagram illustrating an analytical model used in iterative numerical comparison to obtain a simulation algorithm executed by the output signal simulator shown in FIG. 5.

FIG. 11 generally illustrates an analytical model 140 which may be used to correlate relevant input and output signals and convert those signals into a form for comparison and manipulation using system identification. The variable x[n] represents a general input signal into an unknown or poorly-known system 142. In the case of the present invention, the system 142 constitutes the output circuit formed by the output transformer 36 and the isolation capacitors 50 (FIG. 1). In the analytical model 140, the input variable x[n] represents the digital voltage signal 54e and the digital current signal 58e (FIG. 5), represented as $V_{in}[n]$ and $I_{in}[n]$, respectively. The input variables $V_{in}[n]$ and $I_{in}[n]$ are acted upon by the system 142 in a way which can be characterized and identified by an unknown transfer function, which will be identified by iterative numerical comparison system identification techniques.

When the analytical model 140 is used to obtain the simulated output current 107 (FIG. 5), the observed or desired output d[n] is observed and recorded as $I_{out}[n]$. Ultimately once the transfer function has been derived, $I_{out}[n]$ will become the simulated current signal 107 (FIG. 5). The system identification technique illustrated by FIG. 11 has been determined experimentally to provide more accurate results for simulating the output current than for simulating the output voltage of the output transformer 36 and the isolation capacitors 50 of the output circuit of the electrosurgical generator 20 (FIG. 1).

The system identification analytical model 140 employs an adaptive response filter 144. The adaptive response filter 144 possesses the constants of the equations 146 and 147 shown in FIGS. 12 and 13. Each of these constants is determined simultaneously through the iterative numerical comparison process. Referring to FIG. 12, the input variable x[0] is acted upon initially by both the transfer function of the unknown system 142 and the adaptive response filter 144. The unknown system 142 produces the output variable d[0], and the adaptive response filter 144 produces the output variable y[0]. The output variables d[0] and y[0] are compared with each other to produce the error variable e[0]. Based upon the magnitude of the error variable e[0], the adaptive response filter will "adapt" to the next input variable x[n] through numerical analysis, such as least mean squares or recursive least squares analysis, and produce new estimates for the constants of the adaptive response filter 144. Through subsequent iterations [n], [n+1], [n+2], etc., the error variable e[n] should approach zero, indicating that the output variable y[n] and the desired output d[n] are approaching equality. When the error signal e[n] approaches 0, the constants implemented by the adaptive response filter 144 have sufficiently converged to the point that the adaptive response filter 144 then represents a reasonable estimation of the true transfer function of the unknown or poorly-known system 142.

The system identification technique described is computationally intensive and is usually the most expeditiously accomplished by the use of known system identification software, such as MATLAB® software and its "System Identification Toolbox." Such software is employed to derive the constraints implemented by the adaptive response filter 144 as well as to perform the iterative numerical comparison.

Performing the iterative numerical comparison process begins with gathering experimental data. Signals representative of the primary voltage 44, primary current 46 and the output current 24 (FIG. 1) are gathered in a sampling oscilloscope at a very high sample rate, for example 20 million samples per second. The signals representative of the primary voltage 44, the primary current 46 and the output current 24 are obtained and stored for a range of loads typically experienced during electrosurgery, such as within the range or set of 0, 20, 50, 100, and 500 ohms. For each signal representative of the primary voltage 44 in the primary current 46, the individual signals for each of the impedances in the set are concatenated in order of their load. In this manner, the system is treated as a linear time-invariant system where individual responses are concatenated to represent the overall response. To eliminate window multiplication frequencies that could create an adverse influence, a conventional Hanning window is applied to each signal.

After successfully gathering the experimental data in the described manner, the number of poles and zeros which the system identification software will use to model the transfer function is next selected. As shown in FIGS. 12 and 13, the modeling uses six zeros and six poles, as evidenced by the form of the numerators and denominators in the equations of the discrete-time function. A greater or lesser number of zeros or poles can be used. Adding more zeros and poles produces more complex discrete-time functions, but generally increases the accuracy of the function. Alternatively, removing zeros and poles decreases the complexity of the discrete-time function, but at the expense of its accuracy.

The discrete-time, frequency domain function 146 shown in FIG. 12 was obtained by use of the system identification toolbox of MATLAB® software in the manner described above. Using a mathematical transformation, the discrete-time function 146 is transformed to the discrete-time, time-domain function 147 shown in FIG. 13. The derived discrete-time function 147 is an accurate and equivalent representation of the true transfer function of the unknown or poorly-known system 142 (FIG. 12), which in this example is the output transformer 36 and isolation capacitors 50 of the electrosurgical generator 20 (FIG. 1).

Once the discrete-time, time domain function 147 is obtained, that function 147 is programmed into the output current simulator 105 (FIG. 5) as a simulation algorithm. The simulator 105 executes the simulation algorithm when the digital voltage signal 54e and the digital current signal 58e, (shown in FIG. 13 as $V_{in}[n]$ and $I_{in}[n]$, respectively), are supplied to the simulator 105. A calculation using $V_{in}[n]$ and $I_{in}[n]$ as the independent variables of the derived discrete-time function 147 (FIG. 13) produces the output of $I_{out}[n]$, which is the simulated current signal 107 (FIG. 5).

The implementation of the output voltage simulator 104 (FIG. 5) was described using the equivalent circuit 110 (FIG. 7), while the implementation of the current simulator 105 (FIG. 5) has been described using the discrete-time function 147 (FIG. 13). However, an equivalent circuit may also be derived for use by the current simulator 105 (FIG. 5), although the expression for the output current is more complex than the final function 139 (FIG. 10) obtained for the voltage. Similarly, system identification techniques may also be used by the voltage output simulator 104 (FIG. 5). Shown in FIGS. 14 and 15 are the functions or equations 148 and 149 used to arrive at the simulation of the voltage output 23 (FIG. 1). Although the system identification voltage functions 148 and 149 are derived from the original current system identification functions 146 and 147 (FIGS. 12 and 13) by straight-forward substitutions, the accuracy of the voltage output simulation using system identification is dependent upon the mode of operation of the electrosurgical generator (e.g., cut, blend or coagulation) and the load into which the electrosurgical generator delivers the output power.

In the above discussion of using the mathematical algorithms to simulate the voltage signal 106 and the current signal 107 (FIG. 5), the output signal simulators 104 and 105 are described as operating on an instantaneous sampling basis established by the clock frequency of the clock 98 (FIG. 5). However, it is also possible to calculate time averaged or time integrated values, such as root mean square values, from a set of N number of simulation values that are obtained before the respective discrete-time functions 139 (FIG. 10) and 147 (FIG. 13) are employed to derive the simulated signals 106 and 107. The simulation may be performed using any number of sample points. If the simulations are conducted immediately after obtaining each signal 54e and 58e, then the simulated voltage signal 106 and the simulated current signal 107 will represent an instant-related voltage signal 23 and an instant-related current signal 24 (FIG. 1). By obtaining multiple instantaneously-related simulated output values in succession, a continuum of the voltage and current signals 23 and 24 present on the secondary winding 40 of the output transformer 36 (FIG. 1) is obtained.

The simulated output voltage signal 106 and the simulated output current signal 107 are applied to the output value calculator 64, as shown in FIG. 5. The output value calculator 64 is formed by a digital RMS voltage calculator 150, a digital RMS current calculator 152, and a real power average calculator 154a or 154b, all of which are preferably implemented as an array of logic gates. The power average calculator 154a and the power average calculator 154b may be alternatives for one another. By executing numerical algorithms programmed into their logic gates, the calculators 150, 152 and 154a or 154b respectively produce a calculated RMS voltage signal 156 which represents the RMS output voltage 23 of the output signal 22 (FIG. 1), a calculated RMS current signal 158 which represents the RMS output current 24 of the output signal 22 (FIG. 1), and a calculated real power average signal 160 which represents the real power average produced by the output voltage 23 and the output current 24 (FIG. 1) of the output signal 22.

The simulated voltage output signal 106 is applied to the RMS voltage calculator 150 and the simulated output current signal 107 is supplied to the RMS current calculator 152. The simulated voltage and current output signals 106 and 107 are supplied to the power average calculator 154b. In this manner, the calculators 150, 152 and 154b receive the simulated output signals 106 and 107 that represent the actual output voltage 23 and output current 24 of the output signal 22 (FIG. 1). Each of the calculators 150 152, 154a, and 154b receive the clock signal from the clock 98.

The voltage and current calculators 150 and 152 and the real power average calculators 154a and 154b determine root-mean-square (RMS) or average values based upon an N number of samples that are collected during the time that the electrosurgical generator 20 (FIG. 1) is activated, or during a portion of the activation time. The N number of samples collected is determined by the sampling rate established by the clock 98 which drives the dual ADC 96 (FIG. 5). After N number of samples are accumulated, enough values of the simulated output voltage 106 and simulated output current 107 will have been accumulated to allow the calculators 150, 152, 154a and 154b to calculate their respective values over the single time period during which the N samples were accumulated.

Details of the preferred mathematical algorithms executed by the calculators 150, 152, 154a and 154b are generally shown by the mathematical expressions superimposed on the calculators 150, 152, 154a and 154b. The mathematical algorithm executed by the voltage calculator 150 squares each individual sample (n) of the simulated output voltage 106 ($V_{out}$), and then all (N) of the squared samples are summed together. The sum is then divided by the number of samples (N), and the square root is taken. The result is the calculated RMS output voltage value represented by the signal 156. The mathematical algorithm executed by the current calculator 152 squares each individual sample (n) of the simulated output current 107 ($I_{out}$), and then all (N) of the squared samples are summed together. The sum is then divided by the number of samples (N), and the square root is taken. The result is the calculated RMS output current value represented by the signal 158.

The average power is calculated using either of the power average calculators 154a or 154b. The average real power is calculated by the calculator 154a using the instantaneous values of the voltage and current signals 54e and 58e. The product of the voltage and current input signals 54e and 58e, which represent the instantaneous values of the primary voltage 44 and primary current 46 (FIG. 1), produces the real power input of the transformer 36 (FIG. 1). The algorithm implemented by the average power calculator 154a is based upon conservation of energy principles wherein the output power of the transformer 36 (FIG. 1) is equal to the input power minus power losses. The algorithm shown only accounts for the core losses of the transformer 36 (FIG. 1). All power losses, including copper conductor losses, can be accounted for if desired.

Accounting only for the core losses, the power losses of the output transformer 36 (FIG. 1) are given by the following expression:

$$k_{mag} \sum_{n=1}^{N} V_{in}^2[n]$$

where $k_{mag}$ is an empirically measured loss factor derived through experimentation, $V_{in}$ is the input voltage 44 (FIG. 1) applied to the transformer 36 (FIG. 1), and N is the number of samples used in making the power calculation. For an instantaneous output power calculation, N=1. The expression for power losses is based upon negligible values for the primary leakage inductor 116 and the primary leakage resistor 114, and the impedance of the magnetic resistor 118 being small relative to the impedance of the magnetic inductor 120 (FIG. 7). Further, some of the assumptions made for the above power simulation model are based on using the average power calculator 154a for power control when the current and voltages are both relatively small.

The mathematical algorithm executed by the real power average calculator 154a obtains the sum of the difference between the real power input to the transformer and the power losses to the transformer for each of the individual samples. The sum of the differences for the (N) individual samples is divided by (N) to obtain the real power output average. The real power output average is represented by the calculated real power average signal 160.

The mathematical algorithm executed by the real power average calculator 154b multiplies the simulated output voltage signal 106 ($V_{out}$) and the simulated output current signal 107 ($I_{out}$), both of which occur at the simultaneously-related sampling instances (n) of the voltage and current signals. The product of the simulated output voltage and current signals from each simultaneously-related sampling instance (n) is then summed together for the total number of instances (N). The sum is then divided by the number of sampling instances (N). The result is the calculated real power output average represented by the calculated real power average signal 160.

Other algorithms for simulating RMS power, apparent power, imaginary power and other parameters of output power, output voltage or output current can also be implemented.

The calculators 150, 152 and 154a or 154b supply the calculated RMS voltage signal 156, the calculated RMS current signal 158 and the calculated real power signal 160, respectively, to digital sample and hold circuits 162, 164 and 166. The sample and hold circuits 162, 164 and 166 do not alter the signals 156, 158 and 160, but hold the values represented by those signals 156, 158 and 160 when clocked by a signal from the clock 98. The values in the sample and hold circuits are held until replaced by new values. The purpose of the sample and hold circuits 162, 164 and 166 is to ensure that the signals 156, 158 and 160 are available only once every N number of samples. The clock 98 supplies clock signals to the sample and hold circuits 162, 164 and 166 only once each N number of samples. In this regard, the frequency of the signals supplied from the clock 98 to the sample and hold circuits is less than the frequency of the sampling clock signals supplied to the ADC 96 and the simulators 104 and 105. The sample and hold circuits 162, 164 and 166 are part of the analog and digital circuits 62 (FIG. 1).

Figure 16:
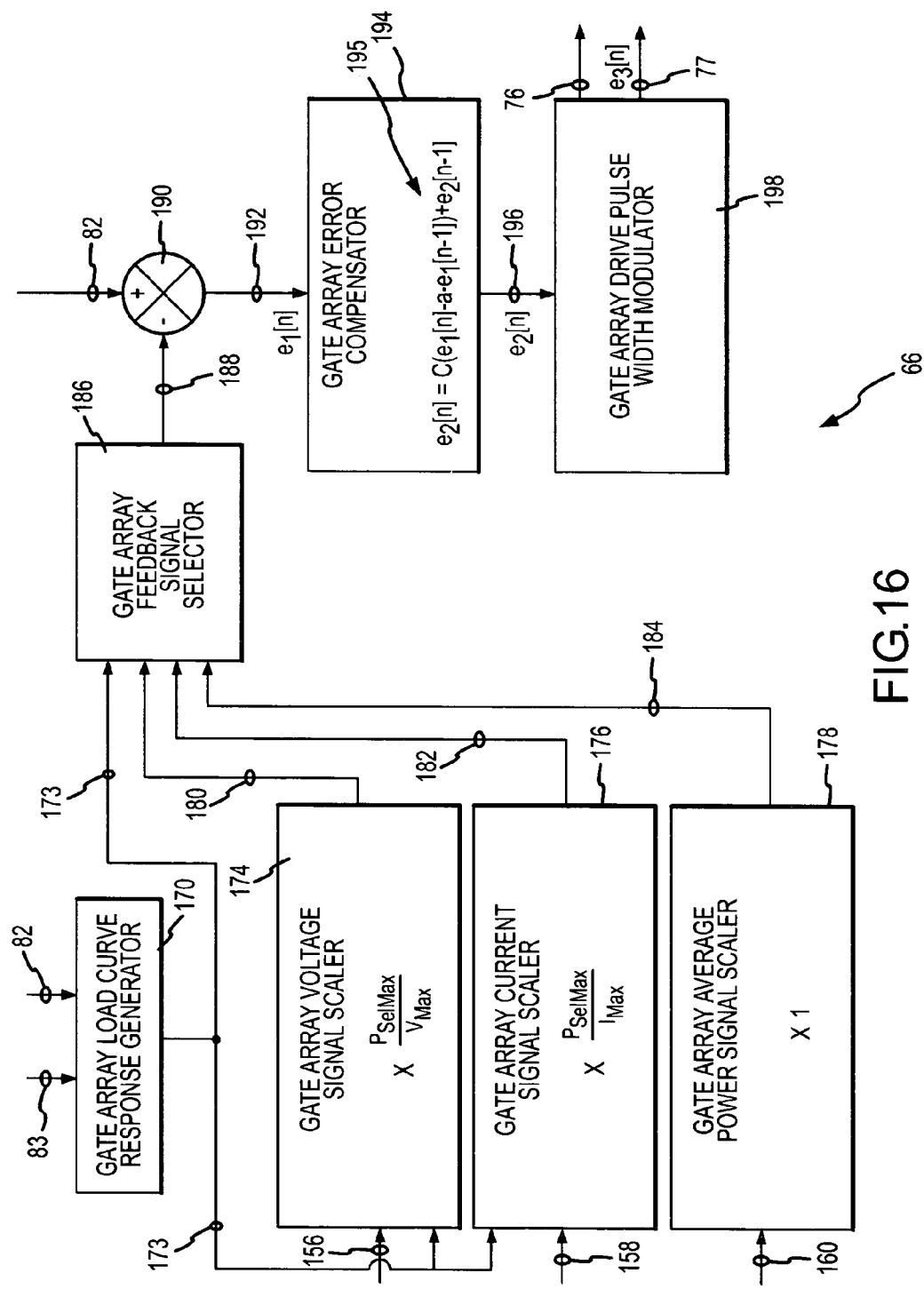
FIG. 16 is a block diagram of an output controller of the control system of the electrosurgical generator shown in FIG. 1.
Figure 17:
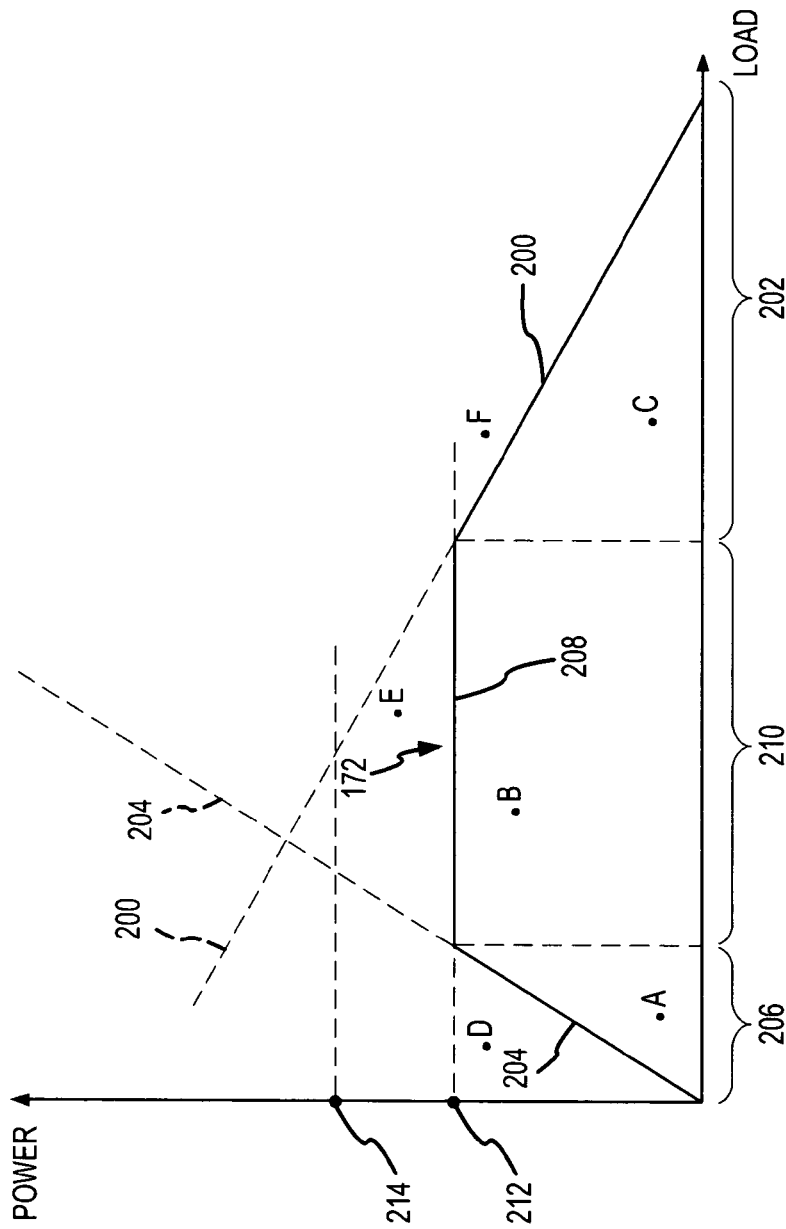
FIG. 17 is a graph of a load curve that is generated by a load curve response generator of the output controller of the output controller shown in FIG. 16.

More details of the output controller 66 of the control system 21 are shown in FIGS. 16 and 17. As shown in FIG. 16, the output controller 66 includes a gate array load curve response generator 170. The load curve response generator 170 establishes and defines a load curve 172 shown in FIG. 17. The load curve 172 is used to limit the power output of the electrosurgical generator 20 (FIG. 1) in relation to the load resistance or impedance of the tissue of the patient 34 (FIG. 1) at the surgical site, and to limit the output power of the electrosurgical generator in relation to the maximum output power for the selected mode of operation selected at the selector controls 80, as represented by the power and mode selection signals 82 and 83 (FIG. 1). The load curve response generator 170 (FIG. 16) generates a load curve signal 173 which contains the mathematical values that define and characterize the load curve 172 (FIG. 17).

The output controller 66 also includes a gate array voltage signal scaler 174, a gate array current signal scaler 176 and a gate array average power signal scaler 178, shown in FIG. 16. The signal scalers 174, 176 and 178 receive the RMS voltage signal ($V_{RMS}$) 156, the RMS current signal ($I_{RMS}$) 158, and the real power average signal ($P_{Ave}$) 160, respectively, from the sample and hold circuits 162, 164 and 166 of the output value calculator 64 (FIG. 5). In addition, the signal scalers 174 and 176 receive the mathematical values of the load curve signal 173.

The signal scalers 174, 176 and 178 scale the values of the signals 156, 158 and 160 based upon the mathematical values which define the load curve 172 to create scaled power signals 180, 182 and 184. The one of the scaled power signals 180, 182, and 184 which has the maximum value is selected by a feedback signal selector 186 and supplied as a feedback signal 188. The selection of the maximum scaled power signal 180, 182 or 184 by the signal selector 186 achieves effective regulation in relation to the load curve 172 (FIG. 17).

The feedback signal 188 is mathematically subtracted from the power selection signal 82 supplied by the selector controls 80 (FIG. 1) by a subtractor 190, and the resulting difference is supplied as a feedback error signal 192. The feedback error signal 192 is supplied to an error compensator circuit 194 which executes a mathematical algorithm represented by a proportional, integral and derivative expression 195 to create a compensated output control signal 196. The proportional, integral and derivative expression 195 executed by the error compensator circuit 194 enables the closed loop system response to be optimized but not unstable from a control theory point of view, and not underdamped, but ensuring a fast step response. The compensated output control signal 196 is supplied to a drive pulse width modulator 198 which adjusts the time width of the on-time of the switch control signal 77 (FIG. 2). As previously discussed, increasing the on-time of the switch control signal increases the amount of energy which is transferred into the resonant circuit 49 (FIG. 1) and thereby increases the energy content of the electrosurgical output signal 22 (FIG. 1). Conversely, decreasing the on-time of the switch control signal 77 (FIG. 2) decreases the amount of energy transferred into the resonant circuit 49 (FIG. 1) and decreases the energy content of the electrosurgical output signal 22 (FIG. 1).

Details concerning the load curve 172 generated by the load curve response generator 170 are shown in FIG. 17. The load curve 172 is defined in relation to a graph which shows the positive and negative power delivered (y-axis) versus the load into which that power is delivered (x-axis). The load into which the power is delivered is the resistance of the tissue of the patient at the surgical site. The characteristics of the load curve 172 vary according to the selected output power and the mode of operation of the electrosurgical generator, as represented by the power and mode selection signals 82 and 83 (FIG. 1). However, in all cases, the load curve has three distinct portions: a constant voltage portion 200, a constant current portion 204, and a constant power portion 208. The mathematical values which define each of the portions of the load curve 172 are therefore variable.

The constant voltage portion 200 of the load curve 172 limits the output voltage to a maximum output voltage $V_{Max}$. As described herein, the maximum output voltage $V_{Max}$ is an RMS voltage, but another voltage characteristic could also be used, such as instantaneous peak voltage. The maximum output voltage $V_{Max}$ is a constant voltage which is the highest voltage that the electrosurgical generator is regulated to deliver for the selected power and mode of operation. Limiting the output voltage in this manner controls the electrosurgical effect according to the selected power and mode of operation. Limiting the maximum output voltage in this manner also prevents excessive and damaging arcing into tissue, especially for the tissue which has a relatively high impedance or resistance. If the voltage was not limited when transferring energy into relatively high impedance or resistance tissue, the arcs would become long, difficult to control and ineffective. Long, difficult to control and ineffective arcs risk damage to adjoining tissue and might risk injury to surgical personnel. Consequently, the maximum output voltage $V_{Max}$ for the electrosurgical generator is established as a constant value, and that maximum output voltage value defines the constant voltage portion 200 of the load curve 172 over the load range 202 of high tissue impedance or resistance.

The constant current portion 204 of the load curve 172 results from limiting the output current to a maximum output current $I_{max}$. As described herein, the maximum output voltage $I_{Max}$ is an RMS current, but another current characteristic could also be used, such as instantaneous peak current. The maximum output current $I_{Max}$ is the highest current that the electrosurgical generator is regulated to deliver in accordance with the selected power and mode. Limiting the maximum output current in this manner prevents excessive and destructive tissue damage from excessive current flow into the tissue, especially for tissue which has a relatively low impedance or resistance in the load range 206. If the current was not limited when transferring energy into relatively low impedance or resistance tissue, that tissue would be severely damaged or destroyed. Limiting the output current in this manner also controls the electrosurgical effect according to the selected power and mode of operation. Consequently, the maximum output current $I_{Max}$ for the electrosurgical generator is established as a constant value, and that maximum current output value defines the constant current portion 204 of the load curve 172 over the range 206 of low tissue impedance or resistance.

The constant power portion 208 of the load curve 172 is effective over a middle load range 210 of tissue impedance or resistance. The constant power portion 208 is applicable when load encountered is greater than the low load range 206 and is less than the high load range 202. The power delivered during from the constant power portion 208 of the load curve 172 is equal to a selected maximum power $P_{SelMax}$ 212 which is established from the selector controls 80 and is represented by the power selection signal 82 (FIGS. 1 and 16).

The selected maximum power $P_{SelMax}$ 212, cannot exceed the maximum power output capability of the electrosurgical generator. The maximum output power capability of the electrosurgical generator is shown by the value at 214. The maximum power output capability of the electrosurgical generator at 214 is a value less than the intersection point of extensions of the constant voltage portion 200 and the constant current portion 204 and is a value greater than the maximum output power which can be selected by the selector controls 80 for a given mode of operation (FIG. 1). Selecting a lower value of output power causes the constant voltage load range 202 and the constant current load range 206 to diminish, which results in an increase in the constant power load range 210. Conversely, selecting a higher value of output power causes the constant voltage load range 202 to increase and the constant current load range 206 to increase, thereby resulting in a decrease in the constant power output range 210.

The load curve shown in FIG. 17 is defined by the slope of the constant voltage portion 200, the slope of the constant current portion 204, and the selected maximum output power portion 208 which is established by the selected maximum output power $P_{SelMax}$ 212. The load curve response generator 170 (FIG. 16) establishes the load curve 172 by mathematical algorithms which define these three portions. The mathematical algorithms which establish the load curve 172 are executed by the array of logic gates which implement the load curve response generator 170 (FIG. 16). The maximum values and selected maximum value $V_{Max}$, $I_{Max}$, and $P_{SelMax}$ which define the load curve 172 (FIG. 17) are supplied by the load curve response generator 170 to the signal scalers 174 and 176, as shown in FIG. 16.

To convert the RMS voltage signal 156 into the scaled power signal 180, the voltage signal scaler 174 multiplies the RMS voltage signal 156 by a scaling factor $P_{selMax}/V_{Max}$. The power $P_{SelMax}$ represents the selected maximum power at 212 of the constant power portion 208 of the load curve 172 (FIG. 17). The voltage $V_{Max}$ represents the constant voltage of the maximum constant voltage portion 200 of the load curve 172 (FIG. 17). The scaled power signal 180 represents the power that is delivered for the value of $V_{RMS}$.

To convert the RMS current signal 158 into the scaled power signal 182, the current signal scaler 176 multiplies the RMS current signal 158 by a scaling factor $P_{SelMax}/I_{Max}$. Again, the power $P_{SelMax}$ represents the selected maximum power at 212 of the constant power portion 208 of the load curve 172 (FIG. 17). The current $I_{Max}$ represents the maximum constant current of the constant current portion 204 of the load curve 172 (FIG. 17). The scaled power signal 182 represents the power that is delivered for the value of $I_{RMS}$.

The RMS power signal 160 is in effect the scaled power signal 184. Therefore, the average power signal scaler 178 multiplies the RMS power signal 160 by scaling factor of 1 to create the scaled power signal 184. The scaled power signal 184 represents the power that is delivered.

The scaled power output signals 180, 182 and 184, and the load curve signal 173 from the load curve response generator 170 are supplied to the feedback signal selector 186. In response, the feedback signal selector 186 executes a mathematical algorithm which compares the magnitudes of the three scaled power signals 180, 182 and 184, and selects the largest one of those three signals to supply as the feedback signal 188. If the largest of these scaled power signals does not exceed the values represented by the load curve 172, the selected feedback signal 188 will result in an increase of power delivered to the resonant circuit 49 to increase the power of the electrosurgical output signal 22 (FIG. 1). Conversely, if one of the three scaled signals 180, 182 or 184 exceeds the values represented by the load curve 172, the final feedback signal 188 will ultimately lead to a reduction in the amount of power of the electrosurgical output signal.

The use of the scaling factors $P_{SelMax}/I_{Max}$ and $P_{SelMax}/V_{Max}$ is one way to generate the final feedback signal 188. Alternatively, the average voltage and current RMS values calculated by the voltage and current signal scalers 174 and 176 can be used directly to obtain the feedback signal without the need of the scaling factors $P_{SelMax}/V_{Max}$ and $P_{SelMax}/I_{Max}$. As discussed above, each of the scaling factors transforms the average RMS voltage or average RMS current to a scaled power value. If the average RMS voltage or average RMS current value exceeds $V_{Max}$ or $I_{max}$, respectively, the scaled power values 180 or 182 obtained by applying the scaling factors will exceed the load curve 172. Alternatively, if the average RMS voltage or average RMS current is less than the load curve 172, the scaled power values 180 or 182 will be less than the load curve 172.

An alternative feedback technique which does not rely upon the scaling factors $P_{SelMax}/I_{Max}$ and $P_{SelMax}/V_{Max}$, can be obtained by assessing whether the average RMS voltage exceeds $V_{Max}$, whether the average RMS current exceeds $I_{Max}$, or whether the average power exceeds $P_{SelMax}$. If any one of the values exceeds its respective predetermined maximum value, then the electrosurgical generator is operating under undesired excessive power conditions and the power output should be decreased. If all of the values does not exceed its respective predetermined maximum value, the electrosurgical generator is failing to deliver the selected maximum output power and the power should be increased. The advantage of using the factors $P_{SelMax}/I_{Max}$ and $P_{SelMax}/V_{Max}$ to create the feedback signal 188 is that only one reference signal, the power selection signal 82 and one error signal 192 are required to implement the control system that is based upon three variables of operation.

The selection of the largest one of the three scaled power signals 180, 182 and 184 causes the regulation of the output power in accordance with the load curve 172, as may be understood by reference to points A-F shown in FIG. 17. Points A-F represent different output power conditions of the electrosurgical generator. Point A is beneath the load curve 172 and represents power output which is less than the desired power output represented at value 212. After the three scaled signals 180, 182 and 184 have been created by the scalers 174, 176 and 178, respectively, the signal 180, 182 or 184 having the largest magnitude is selected as the final feedback signal 188 by the feedback signal selector 186 (FIG. 16). The error signal 192 generated from the final feedback signal 188 ultimately results in an increase of power by increasing the on-time portion of the switch control signal 77 (FIG. 1). A similar situation also exists with respect to points B and C shown in FIG. 17.

A different situation arises for point D which is above the load curve 172 in the constant current range 206. In this case, the current scaled power signal 182 (FIG. 16) will be greater than the maximum permitted current value ($I_{Max}$) because the power delivered at point D is above the constant current portion 204. Because point D is above the constant current portion 204 but below the constant voltage and power portions 200 and 208, multiplication of the average RMS current at point D by the scaling factor $P_{SelMax}/I_{Max}$ in the current signal scaler 176 (FIG. 16) results in a value which exceeds the values for the voltage scaled power signal 180 and the scaled power signal 184 (FIG. 16). Consequently at point D, the feedback signal 188 is derived from the scaled current signal 182 (FIG. 16). The error signal 192 generated from the final feedback signal 188 causes a decrease in output power by decreasing the on-time portion of the switch control signal 77 (FIG. 1).

At point E, which is within the constant power range 210, the power output is above the constant power portion 208 of the curve 172, but is below the constant voltage portion 200 and the constant current portion 204, as shown by the dashed extensions of those portions of the load curve 172. Consequently, the scaling factors $P_{SelMax}/V_{Max}$ and $P_{SelMax}/I_{Max}$ applied by the scalers 174 and 176 do not cause the scaled signals 180 and 182 to exceed the value of the average power scaled signal 184 (FIG. 16), which represents the power at point E. Accordingly, the feedback signal selector 186 selects the average power scaled signal 184 as the signal having the greatest magnitude and supplies that signal as the feedback signal 188. The average power scaled signal 184, being the feedback signal 188, is greater in magnitude than the selected power output represented by the constant power portion 208 of the curve 172 at 212. The resulting error signal 192 causes a reduction in output power by diminishing the on-time portion of the switch control signal 77 (FIG. 1).

The situation with respect to point F is similar to the situation with respect to point D, except that point F is within the constant voltage load range 202. In this case, the scaled signal 180 (FIG. 16) will be greater than the maximum selected power value 212 because the power delivered at point F is above the constant voltage portion 200 but below the constant current and power portions 204 and 208, as shown by the dotted extensions of those portions of the load curve 172. The average RMS voltage corresponding to the value at point F is multiplied by scaling factor of $P_{SelMax}/V_{Max}$ in the voltage signal scaler 174 (FIG. 16), and the result exceeds the value of the scaled current signal 182 and the value of the scaled average power signal 184 (FIG. 16). Consequently at point F, the feedback signal 188 is derived from the voltage scaled power signal 180 (FIG. 16), and the error signal 192 causes a decrease in power output by decreasing the on-time portion of the switch control signal 77 (FIG. 1).

The feedback error determination circuit 190, shown in FIG. 16, is implemented as a subtractor. The value of the maximum selected power ($P_{SelMax}$) is represented by the power selection signal 82, and it is that value from which is subtracted the feedback signal 188. The result of the subtraction is supplied as the error signal 192. The error signal 192 is represented in FIG. 16 as $e_1[n]$.

An error compensator circuit 194, shown in FIG. 16, implements a transfer function. The transfer function is expressed in the discrete-time, frequency-domain (z-domain)

as $H(z)=\copyright (z+a))/(z-1)$, where C is a proportionality constant and "a" is a constant associated with a zero. A discrete-time, time-domain expression 195 is derived from the transfer function and is shown superimposed upon the error compensator circuit 194 which executes the expression 195. In the expression $e_2[n]=C(e_1[n]+a\,e_1[n-1])+e_2[n-1]$, C and "a" are the constants associated with the transfer function, $e_1$ is the error signal 192, and $e_2$ is a compensated error signal which is the output control signal 196.

The output control signal 196 is supplied to the drive pulse width modulator 198. The drive pulse width modulator 198 uses the output control signal 196 $e_2[n]$ to establish or modify the switch control signal 77 (FIG. 2), shown as $e_3[n]$. The magnitude of $e_3[n]$ as the switch control signal 77 determines the on-time 78 (or width) of the next pulse of energy, as previously discussed. The drive pulse width modulator 198 applies a proportioning factor to the output control signal 196 to create the switch control signal 77 (FIG. 2).

The drive pulse width modulator 198 may also use the output control signal 196 $e_2[n]$ as a basis for creating or modifying the power supply control signal 76 (FIG. 1). The power supply control signal 76 may be used to adjust the voltage of the power supply 70 which supplies the current 46 to the resonant circuit 49 (FIG. 1) either in addition to the switch control signal 77 or as an alternative to the switch control signal 77 (FIG. 2), in some cases.

Figure 18:
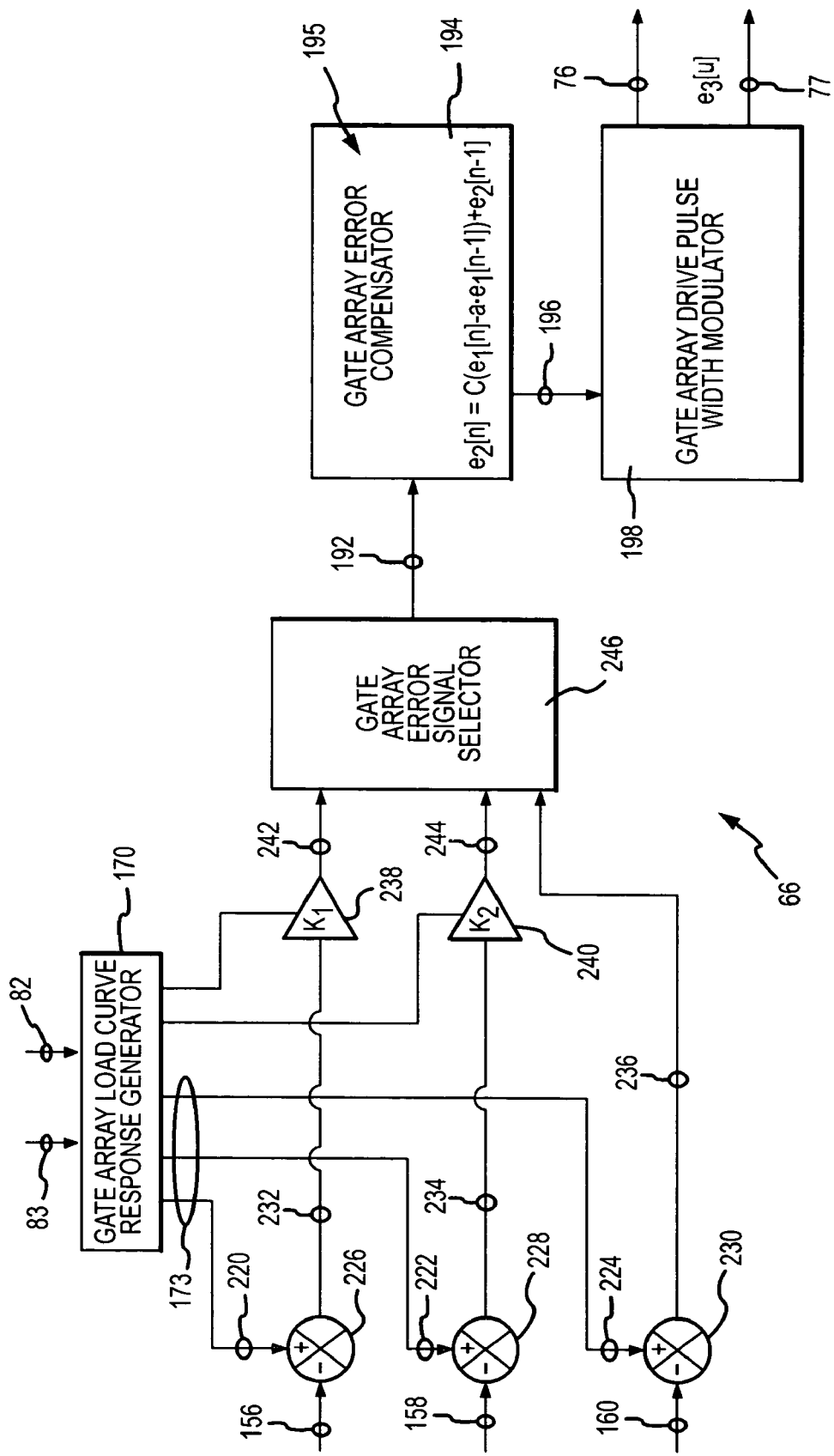
FIG. 18 is a block diagram of an alternative form of the output controller shown in FIG. 16.

Another form of the gate array output controller 66 is shown in FIG. 18. The output controller 66 shown in FIG. 18 is an alternative to the output controller shown in FIG. 16. The output controller 66 shown in FIG. 18 has the benefit of permitting the control loop gain response to be optimized when regulating over the constant voltage and constant current load regions 202 and 206 of the load curve 172 (FIG. 17). It has been determined that different degrees of dampening are typically required to obtain an optimum response when regulating in the constant voltage, the constant current and the constant power portions 200, 204 and 208 of the load curve (FIG. 17). The output controller shown in FIG. 18 has the capability of providing different amounts of gain in all three areas 200, 204 and 208 of the output load curve 172 (FIG. 17), to coordinate with the different degree of dampening.

The RMS voltage signal ($V_{RMS}$) 156, the RMS current signal ($I_{RMS}$) 158 and the calculated real power average signal ($P_{Ave}$) 160 are supplied from the output value calculator 64 (FIG. 5). The gate array load curve response generator 170 supplies the load curve signal 173 which contains the mathematical values that define and characterize the load curve 172 (FIG. 17). Those mathematical values include a signal 220 which represents the maximum output voltage $V_{Max}$ over the maximum constant voltage portion 200 of the load curve 172 (FIG. 17), a signal 222 which represents the maximum output current $I_{max}$ over the constant current portion 204 of the load curve 172 (FIG. 17), and a signal 224 which represents the selected maximum power $P_{SelMax}$ 212 over the constant power portion 208 of the load curve 172 (FIG. 17).

The pairs of signals 156, 220 and 158, 222 and 160, 224 are applied to error determination subtractors 226, 228 and 230, respectively. The signals 220, 222 and 224 are applied to the positive input terminals of the subtractors 226, 228 and 230, respectively, while the RMS voltage signal 156, the RMS current signal 158 and the real power average signal 160 are applied to the negative input terminals of the subtractors 226, 228 and 230, respectively. Each of the subtractors 226, 228 and 230 subtracts the value at the negative terminal from the value at the positive terminal and supply the result as an error signals 232, 234 and 236, respectively.

With the subtractors arranged to mathematically subtract the values in the manner described, whenever one of the signals 156, 158 or 168 exceeds the maximum voltage, maximum current or selected power over the constant voltage, constant current and constant power portions of the load curve, the error signals supplied from the subtractors 226, 228 and 230 are negative in value. Thus, a negative error signal 232, 234 or 236 from any of the subtractors 226, 228 or 230 indicates that an excess of power is delivered in one of the constant voltage 200, constant current 204 and constant power portions 208 of the load curve (FIG. 17), respectively, and a positive error signal 232, 234 or 236 indicates that less than the selected amount of power is delivered.

Because different gains for optimum response are desired when regulating in the constant voltage and constant current portions of the load curve, the error signals 232 and 234 are mathematically multiplied by modification values $K_1$ and $K_2$ at 238 and 240 to thereby increase or decrease the value of the error signals 232 and 234. The modified error signals resulting from the multiplication occur at 242 and 244. The modified error signals 242 and 244 are used to obtain enhanced system control stability in the constant voltage and constant current portions of the load curve 172 (FIG. 17).

The modification values $K_1$ and $K_2$ are adjusted relative to the maximum selected output power represented by the signal 82 and the selected mode of operation represented by the signal 83. The adjustments to the modification values $K_1$ and $K_2$ are based on the characteristics of the load curve 172 (FIG. 17) established by the particular maximum output power and mode selections. Adjusting the modification values $K_1$ and $K_2$ to obtain the modified error signals 242 and 244, achieves the best effect for regulation in the constant voltage and constant power regions of the load curve 172 according to the selected maximum power and selected mode of operation.

The modified error signals 242 and 244 and the error signal 236 are applied to a gate array error signal selector 246. The error signal selector 246 selects the one of the signals 242, 244 or 236 which has the greatest negative value and supplies that signal as the error signal 192. As previously described, a negative signal from the subtractors 226, 228 and 230 indicates an excess of power relative to the load curve, with the greater negative value indicating the greater excess of power. Therefore, the most negative signal selected by the error signal selector 246 represents the maximum error signal 192 which should be used for regulation under circumstances of excessive power delivery. Using the most negative signal 242, 244 or 236 achieves the quickest reduction in excess power output, because the error compensator 194 and drive pulse width modulator 198 reduce the output power based on the greatest amount of error.

On the other hand, as previously described, a positive signal from the subtractors 226, 228 and 230 indicates a deficiency in power relative to the load curve. When the error signal selector 246 selects the most negative of these positive signals, the least positive one of the positive signals is selected. That least positive signal is applied as the error signal 192 to the error compensator 194, and the output control signal 196 causes the pulse width modulator 198 to increase the output power of the electrosurgical generator until the value represented by the selected least positive error signal coincides with the value of the load curve. Thereafter, the same process occurs with respect to the next least positive error signal of the remaining to error signals. The output power is continually adjusted upward in this manner until all three of the positive error signals 242, 244 and 236 coincide with the load curve. Under these conditions, selecting the most negative (least positive) signal 242, 244 or 236 as the error signal 292 for feedback power regulation achieves a power increase, but at a reduced and smoother rate to inhibit overshoot. The logic associated with the error signal selector 246 works because the load curve 172 (FIG. 17) is downwardly concave. If the curve was shaped otherwise, different selection logic would be required.

The selected error signal 192 was applied to the error compensator circuit 194 where it is mathematically manipulated according to the expression 195, in the same manner as has previously been described in FIG. 16. Similarly, the output control signal 196 from the error compensator circuit 194 is applied to the drive pulse width modulator 198 which applies a proportioning factor to create the output control signal 196 in the same manner as has been described in conjunction with FIG. 16. The drive pulse width modulator 198 establishes or modifies the switch control signal 77 to determine the on-time 78 (or width) of the next pulse of energy, as previously discussed. The drive pulse width modulator 198 may also supply the power supply control signal 76 to control the power supply 70 (FIG. 1) in the same manner to power supply 70 (FIG. 1), as has been previously described.

All the components and functionality of both forms of the output controller 66 (FIGS. 1, 16 and 18) are preferably implemented in an array of logic gates. The techniques of error measurement and selection described in conjunction with FIGS. 16 and 18 are two of many that could be implemented. Other techniques such as fading from one limit to another using an S-curve mathematical function at each limit changeover, are also possible. However, techniques described achieve very rapid control when implemented by executing the mathematical algorithms programmed in the array of logic gates.

The output power of the electrosurgical generator can be adjusted according to many different criteria, as previously discussed. In another method to adjust the output power, a gate array drive voltage modulator (not shown) converts the output control signal 196 $e_2[n]$ into a low impedance voltage source signal, $e_{3Voltage}[n]$, that is supplied to the base of a bipolar junction transistor (not shown) which forms the switch 72 (FIG. 1), thereby biasing the bipolar junction transistor. The amount of bias supplied to the bipolar junction transistor affects the current 46 conducted through that bipolar junction transistor and consequently affects the amount of current 46 conducted into the resonant circuit 49 (FIG. 1), thereby increasing the output power.

One of the benefits of the present invention is accurately simulating the output voltage 23 and the output current 24 for feedback power control without connecting sensors on the secondary winding 40 of the output power transformer 36, which is the situation shown in FIG. 1. Instead, by accurately and reliably simulating the output voltage 23 and the output current from signals obtained from the primary winding 38, the adverse influences on the output signal formed by the sensors is avoided entirely. The simulation using the signals obtained from the primary winding corrects for distortions induced by the output transformer 36 without introducing further distortions caused by sensors connected to the secondary winding 40. Connecting output voltage and current sensors to the secondary winding of the output transformer has the effect of degrading the quality of the electrosurgical output signal and also has the effect of increasing leakage current, as well as diminishing the available power for use in electrosurgery. However, in those cases where simulation of the output voltage 23 and output current 24 from signals obtained from the primary winding is not desired or used, as is the case in the electrosurgical generator 250 shown in FIG. 19, the simulation is still useful to enhance the accuracy of the sense signals. The simulation reduces or eliminates the distortions introduced by the output voltage and output current sensors. Such sensors are typically sensing transformers whose distortions can be essentially eliminated by use of the simulation algorithms described above. The logic gate controller 21 and other aspects of the present invention are equally applicable to that type of electrosurgical generator 250.

Figure 19:
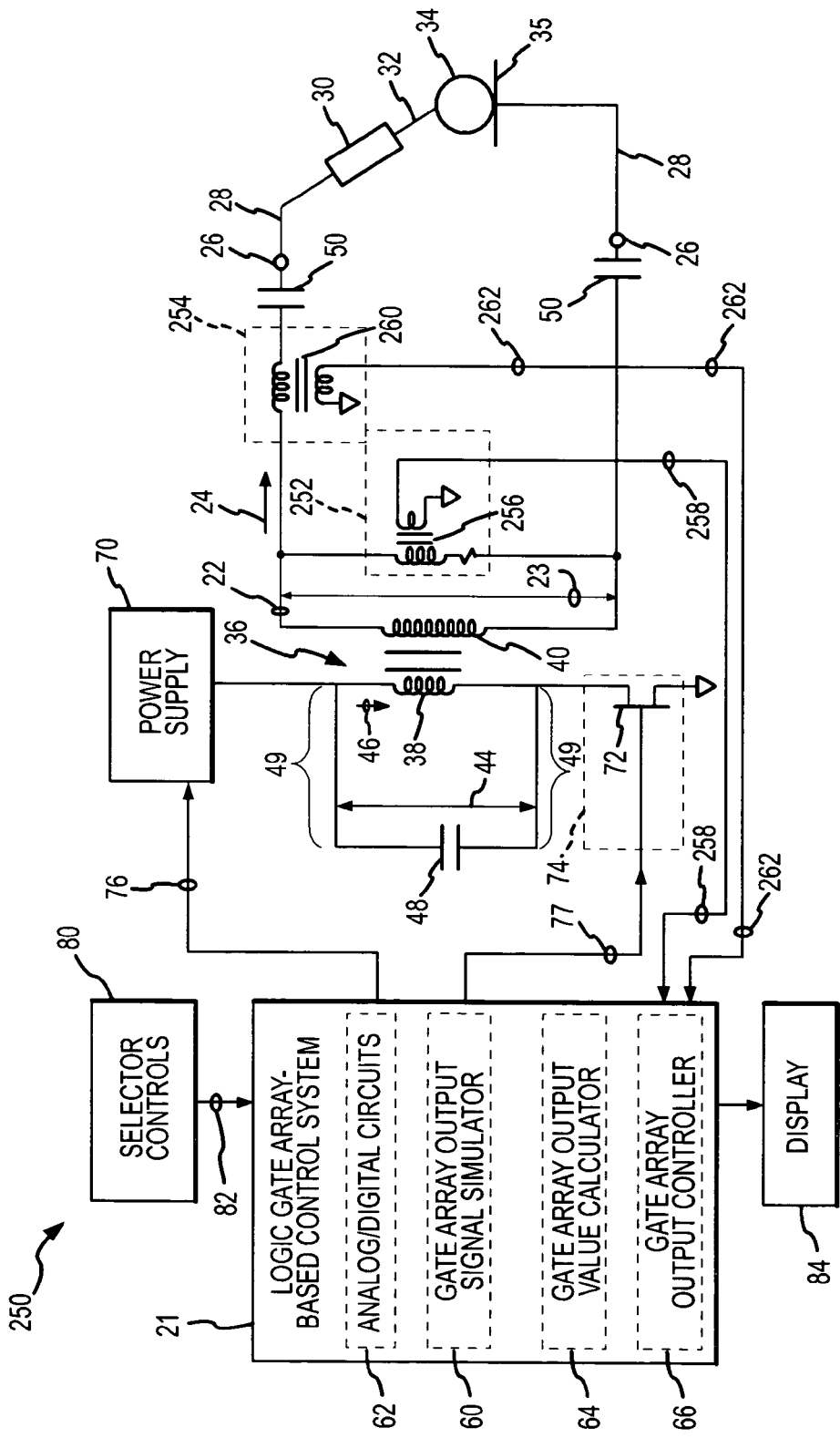
FIG. 19 is a block diagram of another electrosurgical generator which incorporates the present invention.

The electrosurgical generator 250, shown in FIG. 19, uses the logic gate controller 21 and many of the same components as have been described in connection with the electrosurgical generator 20 shown in FIG. 1, except that the electrosurgical generator 250 does not simulate the output voltage 23 and the output current 24 by sensing the primary voltage 44 and primary current 46. Instead, the electrosurgical generator 250 uses an output voltage sensor 252 and an output current sensor 254 to sense directly the output voltage 23 and the output current 24. The output voltage sensor 252 is connected in parallel with the secondary winding 40, and the output current sensor 254 is connected in series with the conductor 28 from the secondary winding 40. The voltage sensor 252 uses a transformer 256 to produce a reduced level voltage sense signal 258. Similarly, the output current sensor 254 uses a transformer 260 to develop a current sense signal 262 which represents the output current 24.

The voltage sense signal 258 and the current sense signal 262 are supplied directly to the system controller 21. Since both transformers 256 and 260 are subject to many of the high-frequency high-voltage influences that affect the output transformer 36, those influences combine with the inherent distortions created by an actual transformer to cause the actual characteristics of the sense signals 258 and 262 to depart from those of an ideal transformer. To counter these distortions, the voltage and current sense signals 258 and 262 are supplied to the output signal simulator 60 of the control system 21 to obtain simulated output sense signals which accurately and truly represent the output voltage 23 and the output current 24. The output signal simulator 60 corrects for distortions induced by the transformers 256 and 260. The simulated output voltage and current signals 258 and 262 from the sensors 252 and 254 therefore more accurately represent the output voltage 23 and output current 24, and provide an enhanced opportunity for the electrosurgical generator 250 to operate in an improved manner in the very demanding electrosurgical environment where high-voltage and high-frequency signals must be derived accurately and utilized quickly.

The present invention obtains a very effective closed loop feedback control system for an electrosurgical generator by the advantageous use of an array of programmable logic gates, such as a field programmable gate array (FPGA). The logic gates are capable of rapidly processing signals. The logic gates allow the derivation and mathematical manipulation of the electrosurgical output voltage and current signals on a near-instantaneous basis, due to the speed at which logic gates are capable of processing signals. The near-instantaneous computations permit the control system to calculate and regulate least one parameter of the output signal 22, such as real output power, RMS output current, RMS output voltage and apparent output power, on a near-instantaneous basis. Regulating on the basis of real power is considerably more complex and computationally intensive if attempted by non-gate array implementations, and the system response times will be considerably slower. The array of logic gates more accurately controls and regulates the power, voltage, current and other parameters related to those values during electrosurgery, compared to other implementations of control systems.

The significance of these and other improvements and advantages will become apparent upon gaining a full appreciation of the ramifications and improvements of the present invention. Preferred embodiments of the invention and many of its improvements have been described with a degree of particularity. The detail of the description is of preferred examples of implementing the invention. The detail of the description is not necessarily intended to limit the scope of the invention. The scope of the invention is defined by the following claims.

The invention claimed is:

1. An electrosurgical generator having a control system which comprises an array of logic gates programmed to execute mathematical algorithms for regulating at least one parameter of output power, output voltage or output current of a radio frequency electrosurgical output signal in a closed loop feedback response to digital samples of sensed instantaneous values of the output voltage and the output current in cycles of the output signal.

2. An electrosurgical generator as defined in claim 1, wherein the programmed algorithms executed by the array of logic gates simulate the values of the output voltage and output current in response to values derived other than by directly sensing the values of output voltage and output current.

3. An electrosurgical generator as defined in claim 1, which comprises a power output transformer which has a primary winding to which primary voltage and primary current are applied, and a secondary winding from which the electrosurgical output signal is supplied; and wherein the programmed algorithms executed by the array of logic gates simulate the values of the output voltage and output current in response to values of the primary voltage and primary current sensed at the primary winding.

4. An electrosurgical generator as defined in claim 3, which comprises a resonant circuit which includes the primary winding, and a driver circuit which charges the resonant circuit with energy in response to an energy charging signal; and wherein the programmed algorithms executed by the array of logic gates adjust characteristics of the energy charging signal.

5. An electrosurgical generator as defined in claim 1, wherein the programmed algorithms executed by the array of logic gates are numerical calculations.

6. An electrosurgical generator as defined in claim 1, wherein the parameter for regulation is power.

7. An electrosurgical generator as defined in claim 6, wherein the parameter for regulation is real power.

8. An electrosurgical generator as defined in claim 7, wherein the programmed algorithms executed by the array of logic gates derive positive and negative values of the output voltage and the output current at simultaneously-related instants and calculate positive and negative values of output power from the values of the output voltage and output current.

9. An electrosurgical generator as defined in claim 8, wherein the instantaneous positive and negative values of the output voltage and output current are simulated by the programmed algorithms executed by the array of logic gates.

10. An electrosurgical generator as defined in claim 8, wherein the programmed algorithms executed by the array of logic gates calculate the real power output of the electrosurgical output signal by multiplying each instance of the positive and negative values of the output voltage and output current.

11. An electrosurgical generator as defined in claim 10, wherein the programmed algorithms executed by the array of logic gates define an output load curve of output power relative to load resistance into which the output power is delivered.

12. An electrosurgical generator as defined in claim 11, wherein the array of logic gates is further programmed to define the output load curve in response to a selected maximum power output from the electrosurgical generator and a selected mode of operation of the electrosurgical generator.

13. An electrosurgical generator as defined in claim 11, wherein the programmed algorithms executed by the array of logic gates derive a feedback error signal by comparison of the output load curve and the calculated real power output.

14. An electrosurgical generator as defined in claim 13, wherein the programmed algorithms executed by the array of logic gates proportions, integrates and differentiates the feedback error signal to create a compensated signal for regulating real power of the electrosurgical output signal.

15. An electrosurgical generator as defined in claim 11, wherein:
the output load curve includes a constant current portion having a maximum output current value and a constant voltage portion having a maximum output voltage value;
the programmed algorithms executed by the array of logic gates calculate an average value of output voltage and an average value of average output current by direct calculation using each instance of the positive and negative values of the output voltage and output current, respectively;
the programmed algorithms executed by the array of logic gates scale the average value of output voltage into a scaled average output voltage value by multiplying the average value of output voltage by a constant equal to the selected maximum power output divided by the maximum output voltage value;
the programmed algorithms executed by the array of logic gates scale the average value of output current into a scaled average output current value by multiplying the average value of output current by a constant equal to the selected maximum power output divided by the maximum output current value; and
the programmed algorithms executed by the array of logic gates derive a feedback signal by selection of one of the calculated real power output, the scaled average output voltage value or the scaled average output current value which has a predetermined magnitude relative to the others.

16. An electrosurgical generator as defined in claim 11, wherein:
the output load curve includes a constant voltage portion having a maximum output voltage value, a constant current portion having a maximum output current value and a constant power portion having a maximum selected output power;
the programmed algorithms executed by the array of logic gates calculate an average value of output voltage, an average value of average output current and an average value of the real output power by direct calculation using each instance of the positive and negative values of the output voltage, of the positive and negative values of the output current and of the positive and negative values of the real output power;
the programmed algorithms executed by the array of logic gates mathematically subtract the average value of output voltage from the maximum selected output voltage value to obtain a first error signal;
the programmed algorithms executed by the array of logic gates mathematically subtract the average value of output current from the maximum selected output current value to obtain a second error signal;
the programmed algorithms executed by the array of logic gates mathematically subtract the average value of the real output power from the maximum output voltage value to obtain a third error signal; and
the programmed algorithms executed by the array of logic gates derive a feedback signal by selection of a one of the first, second or third error signals having the a predetermined relative magnitude with respect to the other error signals.

17. An electrosurgical generator as defined in claim 16, wherein the programmed algorithms executed by the array of logic gates scales the first and second error signals, and the selection to derive the feedback error signal is with respect to the first scaled error signal, the second scaled error signal or the third error signal.

18. A method for regulating at least one parameter of output power, output voltage or output current of a radio frequency output electrosurgical signal by executing mathematical algorithms programmed into an array of logic gates which define a closed loop feedback response to digital samples of sensed instantaneous values of the output voltage and the output current in cycles of the output signal.

19. A method as defined in claim 18, further comprising executing the programmed algorithms by numerical calculations.

20. A method as defined in claim 18, wherein the parameter for regulation is power.

21. A method as defined in claim 20, wherein the parameter for regulation is real power.

22. A method as defined in claim 21, further comprising executing the programmed algorithms to simulate positive and negative values of the output voltage and output current at simultaneously-related instants from values of the output voltage and the output current obtained other than from sensing the output voltage and the output current of the output signal.

23. A method as defined in claim 22, further comprising executing the programmed algorithms to calculate the real power output of the electrosurgical output signal by multiplying each instance of the positive and negative sensed values of the output voltage and output current.

24. A method as defined in claim 23, further comprising executing the programmed algorithms to:
define an output load curve of real output power in relation to load resistance into which the output power is delivered and in relation to a selected maximum power output from the electrosurgical generator;
derive a feedback signal by comparison of the output load curve and the calculated real power output;
derive an error signal by comparison of the feedback signal and the selected maximum power output; and
proportion, integrate and differentiate the error signal to create a compensated signal; and
use the compensated signal to regulate the real power of the electrosurgical output signal.

25. An electrosurgical generator which delivers an output electrosurgical signal and has a closed loop control system which comprises an output signal simulator which calculates simulated values representative of output voltage and output current of the output signal, and an output value calculator which calculates parameter values from the simulated values wherein the parameter values relate to at least one parameter of output power or output voltage or output current of the output signal, and an output controller which calculates a feedback error signal and a control signal from the parameter values wherein the control signal regulates at least one parameter of output power or output voltage or output current of the output signal; and wherein the calculations are performed by mathematical algorithms executed by the output signal simulator, the output value calculator and the output controller; and wherein the output signal simulator and the output value calculator comprise an array of logic gates programmed to execute the mathematical algorithms of the output signal simulator and the output value calculator.

26. An electrosurgical generator as defined in claim 25, wherein the programmed algorithms executed by the array of logic gates of the output signal simulator simulate the values of the output voltage and output current in response to signals derived other than by directly sensing the values of output voltage and output current of the output signal.

27. An electrosurgical generator as defined in claim 25, which comprises a power output transformer which has a primary winding to which primary voltage and primary current are applied, and a secondary winding from which the electrosurgical output signal is supplied; and wherein the programmed algorithms executed by the array of logic gates of the output signal simulator simulate the values of the output voltage and output current in response to values of the primary voltage and primary current sensed at the primary winding.

28. An electrosurgical generator as defined in claim 27, which comprises a resonant circuit which includes the primary winding, and a driver circuit which charges the resonant circuit with energy in response to an energy charging signal; and wherein the control signal adjusts characteristics of the energy charging signal.

29. An electrosurgical generator as defined in claim 25, wherein the programmed algorithms executed by the array of logic gates of the output signal simulator and the output value calculator are numerical calculations.

30. An electrosurgical generator as defined in claim 25, wherein the parameter for regulation is power.

31. An electrosurgical generator as defined in claim 30, wherein the parameter for regulation is real power.

32. An electrosurgical generator as defined in claim 31, wherein the programmed algorithms executed by the array of logic gates of the output value calculator derive positive and negative values of the output voltage and the output current at simultaneously-related instants and calculate positive and negative values of output power from the values of the output voltage and output current.

33. An electrosurgical generator as defined in claim 32, wherein the instantaneous positive and negative values of the output voltage and output current are simulated by the programmed algorithms executed by the array of logic gates of the output signal simulator.

34. An electrosurgical generator as defined in claim 32, wherein the programmed algorithms executed by the array of logic gates of the output signal simulator calculate the real power output of the electrosurgical output signal by multiplying each instance of the positive and negative sensed values of the output voltage and output current.

35. An electrosurgical generator as defined in claim 32, wherein the output controller defines an output load curve of output power relative to load resistance into which the output power is delivered and in response to a selected maximum power output from the electrosurgical generator and a selected mode of operation of the electrosurgical generator; and the output controller derives a feedback error signal by comparison of the output load curve and the calculated real power output.

36. An electrosurgical generator as defined in claim 35, wherein the output controller proportions, integrates and differentiates the feedback error signal to create a compensated signal for regulating real power of the electrosurgical output signal.

37. An electrosurgical generator as defined in claim 25, wherein the output controller comprises an array of logic gates programmed to execute the mathematical algorithms of the output controller.

* * * * *